(12) United States Patent
Mlekicki et al.

(10) Patent No.: US 9,800,328 B2
(45) Date of Patent: Oct. 24, 2017

(54) SYSTEMS AND METHODS FOR OXYGEN SENSING

(71) Applicant: New York University, New York, NY (US)

(72) Inventors: Filip Mlekicki, Brooklyn, NY (US); Alexey Sidelev, Mamoroneck, NY (US); Gamal Khalil, Redmond, WA (US); Masoud Ghandehari, Rumson, NJ (US); Mohsen Hossein, Hoboken, NJ (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/982,275

(22) Filed: Dec. 29, 2015

(65) Prior Publication Data

US 2016/0187258 A1  Jun. 30, 2016

Related U.S. Application Data

(60) Provisional application No. 62/097,818, filed on Dec. 30, 2014.

(51) Int. Cl.
*H04B 10/07* (2013.01)
*G01N 21/27* (2006.01)
(Continued)

(52) U.S. Cl.
CPC ........... *H04B 10/07* (2013.01); *G01N 21/274* (2013.01); *G01N 21/278* (2013.01);
(Continued)

(58) Field of Classification Search
CPC ............... G01N 21/274; G01N 21/278; G01N 21/6408; G01N 21/7703; G01N 2021/772;
(Continued)

(56) References Cited

U.S. PATENT DOCUMENTS

| 6,921,546 B2 | 7/2005 | Albach |
| 2004/0083793 A1 | 5/2004 | Susko |

(Continued)

OTHER PUBLICATIONS

American Society for Testing and Materials, Standard Guide for Direct-Push Water Sampling for Geoenvironmental Investigations, Jan. 1997, 14 pages.
(Continued)

*Primary Examiner* — Mark R Gaworecki
(74) *Attorney, Agent, or Firm* — Foley & Lardner LLP

(57) ABSTRACT

An oxygen sensing system comprises a substrate structured to communicate optical signals. An oxygen sensing layer is disposed on the substrate and comprises an oxygen sensing molecule in a matrix in a first unexcited state and formulated to: (a) be excited by a first optical signal to move to a second state; (b) be quenched in the second state by oxygen; and (c) emit a second optical signal corresponding to an amount of oxygen. A protective layer, disposed on the oxygen sensing layer, includes at least one of i) an oleophobic layer and ii) an anti-fouling layer. A controller is optically coupled to the substrate and structured to generate the first optical signal, receive the second optical signal and determine oxygen concentration from the second optical signal.

24 Claims, 13 Drawing Sheets

(51) Int. Cl.
*G01N 21/64* (2006.01)
*G01N 21/77* (2006.01)

(52) U.S. Cl.
CPC ..... *G01N 21/6408* (2013.01); *G01N 21/7703* (2013.01); *G01N 2021/772* (2013.01); *G01N 2021/773* (2013.01); *G01N 2021/7759* (2013.01); *G01N 2021/7786* (2013.01); *G01N 2201/1211* (2013.01)

(58) Field of Classification Search
CPC ..... G01N 2021/773; G01N 2021/7759; G01N 2021/7786; G01N 2201/1211; H04B 10/07
See application file for complete search history.

(56) References Cited

U.S. PATENT DOCUMENTS

| | | | |
|---|---|---|---|
| 2004/0115823 A1 | 6/2004 | Potyrailo | |
| 2007/0122311 A1 | 5/2007 | Shahriari | |
| 2010/0278771 A1 | 11/2010 | Lobe et al. | |
| 2012/0080613 A1* | 4/2012 | Kingsley | C09K 11/025 250/459.1 |
| 2014/0371553 A1 | 12/2014 | Winkelman | |

OTHER PUBLICATIONS

CLU-IN, Passive (no purge) Samplers, U.S. EPA Contaminated Site Cleanup Information (CLU-IN), Apr. 22, 2014, 13 pages.

In-Situ Inc., Frequently Asked Questions: EPA-Approved In-Situ® Inc. Optical Rugged Dissolved Oxgyen (RDO®) Sensor, Technical Note, Jan. 2013, 6 pages.

International Search Report and Written Opinion for PCT Application No. PCT/US2015/067806, mail date Mar. 4, 2016, 9 pages.

Li, et al., Evaluation of Subsurface Oxygen Sensors for Remediation Monitoring, Groundwater Monitoring & Remediation, vol. 16, No. 1, Winter 1996, 6 pages.

Panahi, A., Fiber Optic Oxygen sensor using Fluorescence Quenching for aircraft inerting fuel tank applications, Photonics in the Transportation Industry: Auto to Aerospace II, Proc. of SPIE, vol. 7314, 73140D-2, May 2009, 12 pages.

Patterson, et al., An In Situ Device to Measure Oxygen in the Vadose Zone and in Ground Water: Laboratory Testing and Field Evaluation, Ground Water Monitoring & Remediation, vol. 28, No. 2, Spring 2008, 7 pages.

Pollack, et al., Electrowetting-based actuation of droplets for integrated microfluidics, Lab on a Chip, vol. 2, May 2002, retrieved from the Internet at http://www.biophysik.physik.uni-muenchen.de/download/biopheinf/seminar/Fair_LOC_2002.pdf on Feb. 23, 2016, 2016, pp. 96-101, 6 pages.

Tang, et al., Hybrid xerogel films as novel coatings for antifouling and fouling release, Biofouling: The Journal of Bioadhesion and Biofilm Research, vol. 21, No. 1, Feb. 1, 2005, 13 pages.

U.S. Environmental Protection Agency, Chapter V: Direct Push Technologies, Expedited Site Assessmnet Tools for Underground Storage Tank Sites: A Guide for Regulators, Mar. 1997, 68 pages.

YSI, Inc., The Evolution of Water Quality Monitoring, eBook, YSI Water Quality Monitoring Systems, Sep. 29, 2015, 54 pages.

* cited by examiner

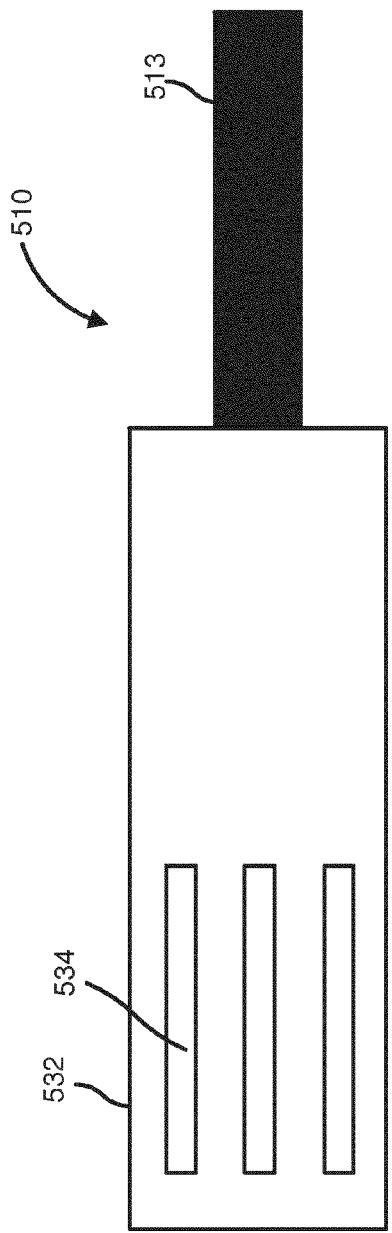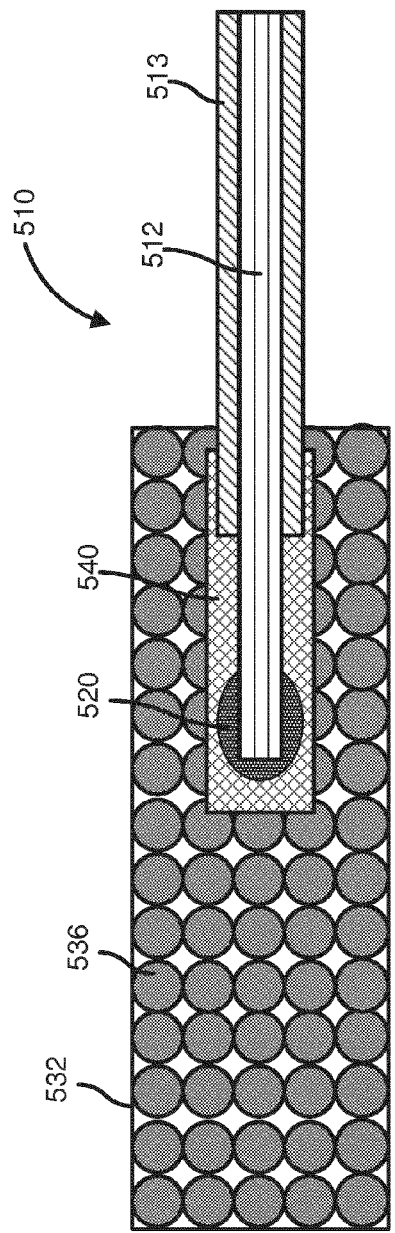
FIG. 6A
FIG. 6B

SYSTEMS AND METHODS FOR OXYGEN SENSING

CROSS-REFERENCE TO RELATED APPLICATIONS

This application claims priority to and benefit of U.S. Provisional Patent Application No. 62/097,818, filed Dec. 30, 2014 and entitled "Oxygen Sensor," the entire disclosure of which is incorporated herein by reference.

This invention was made with government support under "National Institute of Health (NIH) Small Business Technology Transfer Grant (STTR)," Program Award Number 1R41ES023250-01 awarded by the National Institute of Environmental Health Sciences (NIEHS). The government has certain rights in the invention.

TECHNICAL FIELD

The present disclosure relates generally to optical sensors.

BACKGROUND

Sensors for determining the concentration of oxygen in a gas or a fluid find applications in a variety of fields such as environmental monitoring, food safety, and biomedical diagnostic applications. For example, environmental remediation projects often involve subsurface oxygen measurements in aqueous samples. Oxygen sensing can also be used in water quality testing as an indicator of microbial activity or presence of toxins. Similarly, oxygen sensors can be used in biomedical diagnostic applications, for example, to measure blood oxygen level. Other applications include food science, agricultural applications, surface, aquaculture, surface, storm and waste water monitoring, aerobic processes, energy exploration, production and distribution, renewable energy, transportation, fundamental research, etc.

Conventional sensors for measuring oxygen generally include electrochemical sensors. These sensors work on the principle that oxygen reduces on the surface of an electrode that is polarized at a sufficiently negative voltage. The reduction produces a current a magnitude of which is proportional to the concentration of the oxygen in a sample which is being tested (e.g., an environmental, food or biomedical sample). Such electrochemical sensors generally have to be regularly calibrated and can suffer from drift.

Furthermore conventional oxygen sensors can have a short life and can be susceptible to damage by organic solvents or hydrocarbons which can be present in the sample. For example, the field of enhanced aerobic bioremediation utilizes microorganisms already present in the soil to naturally decompose dangerous contaminants. Such contaminants can include hydrocarbons and/or organic solvents which contaminate sub-surface soil and water. Success of such bioremediation projects depend on maintaining an adequate level of dissolved oxygen in the sub-surface soil and water samples. Thus, in-situ, real time and long term measurement of dissolved oxygen in such sub-surface samples is critical in ensuring the success of enhanced bioremediation projects.

SUMMARY

Embodiments described herein relate generally to optical sensors, and in particular to fiber optic oxygen sensors that include an oxygen sensitive dye suspended in a matrix and over coated with a protective layer, preventing fouling of such sensors and in-situ calibration thereof.

In some embodiments, an oxygen sensing system comprises a substrate structured to communicate optical signals. An oxygen sensing layer is disposed on the substrate. The oxygen sensing layer comprises an oxygen sensing molecule disposed in a matrix. The oxygen sensing molecule is formulated to be in a first unexcited state. The oxygen sensing molecule is further formulated to: (a) be excited in response to a first optical signal to move to a second state; (b) be quenched in the second state by oxygen present in a sample in contact with the oxygen sensor; and (c) emit a second optical signal different from the first optical signal. An optical parameter of the second optical signal corresponds to an amount of oxygen present in the sample.

A protective layer is disposed on the oxygen sensing layer. The protective layer includes at least one of i) an oleophobic layer configured to protect the oxygen sensing layer from hydrocarbons and organic solvents, and ii) an anti-fouling layer configured to protect the oxygen sensing layer from fouling.

A controller is optically coupled to the substrate. The controller is structured to generate the first optical signal and communicate the first optical signal to the oxygen sensing layer via the substrate. The controller is further configured to receive the second optical signal via the substrate and analyze the optical parameter of the second optical signal to determine a concentration of the oxygen in the sample.

In some embodiments, an oxygen sensor comprises a substrate structured to communicate optical signals. An oxygen sensing layer is disposed on the substrate. The oxygen sensing layer comprises an oxygen sensing molecule disposed in a matrix. The oxygen sensing molecule is formulated to be in a first unexcited state. The oxygen sensing molecule is further formulated to: (a) be excited in response to a first optical signal to move into a second state, (b) be quenched in the second state by oxygen present in a sample in contact with the oxygen sensor, and (c) emit a second optical signal different from the first optical signal. An optical parameter of the second optical signal corresponds to an amount of the oxygen present in the sample. A protective layer is disposed on the oxygen sensing layer. The protective layer includes at least one of i) an oleophobic layer configured to protect the oxygen sensing layer from hydrocarbons and organic solvents, and ii) an anti-fouling layer configured to protect the oxygen sensing layer from fouling.

In some embodiments, a method for calibrating an oxygen sensor which includes an oxygen sensing layer positioned on a first substrate includes positioning a calibration device proximate to the oxygen sensor. The calibration device includes a second substrate structured to communicate a calibrant optical signal. A calibrant layer is positioned on at least a portion of the second substrate. A calibrant optical signal is communicated through the second substrate so as to urge the calibrant layer to at least one of release a predetermined amount of heat, release a predetermined amount of oxygen, or scavenge oxygen in proximity of the oxygen sensor. At least one of a temperature calibration value, a higher calibration parameter or a lower calibration parameter is determined. The oxygen sensor is calibrated based on at least one of the temperature calibration value, the higher calibration parameter or the lower calibration parameter.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 6A is a side view and FIG. 6B is a side cross-section view of an oxygen sensing assembly which includes an oxygen sensor positioned within an internal volume of a housing that also includes a plurality of anti-fouling particles positioned within the internal volume.

Figure 1:
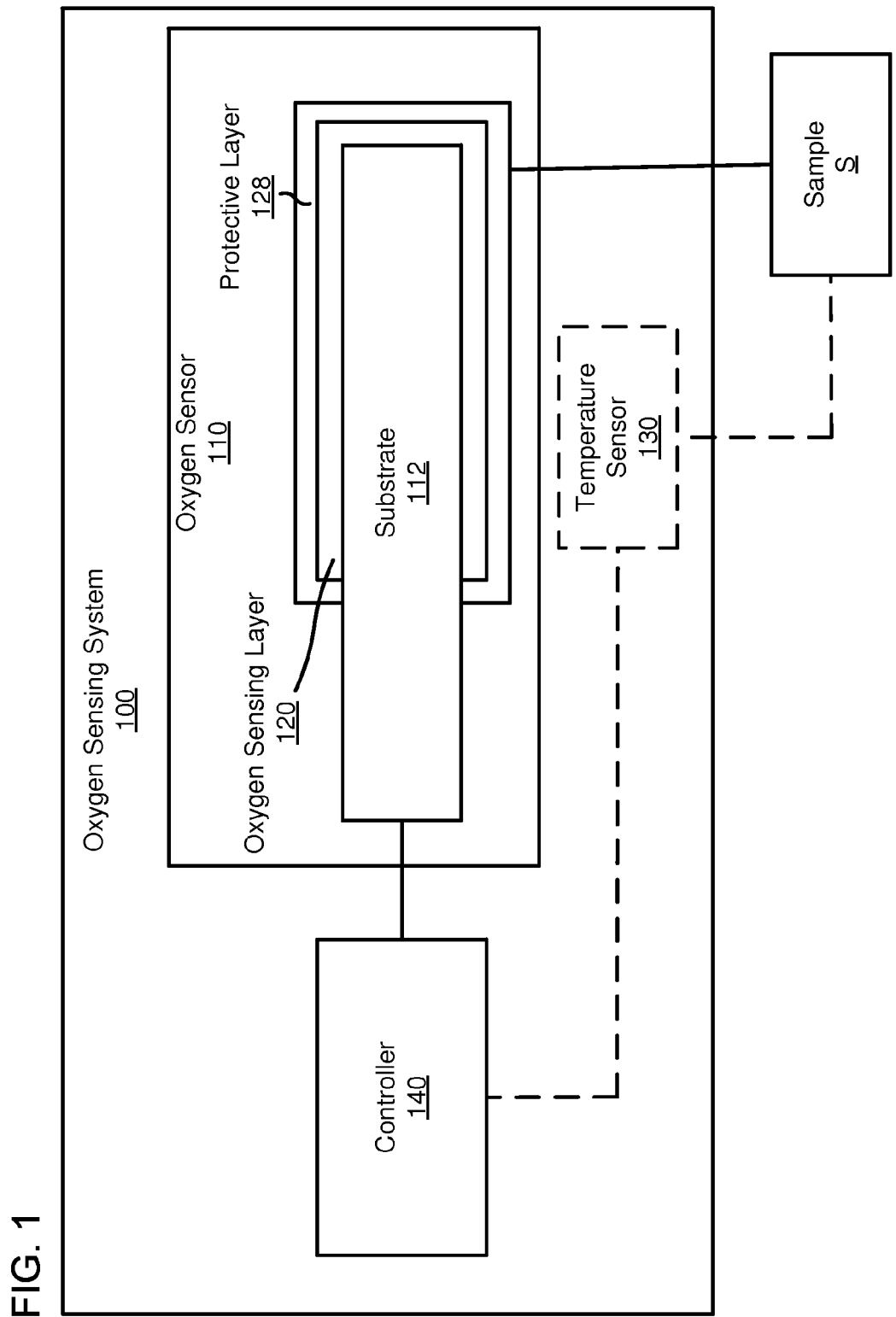
FIG. 1 is a schematic block diagram of an oxygen sensing system, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to optical oxygen sensors, and in particular to fiber optic oxygen sensors that include an oxygen sensitive dye suspended in a matrix and over coated with a protective layer, preventing fouling of such sensors and in-situ calibration thereof.

Embodiments of the oxygen sensing system described herein provide several benefits including, for example: (1) performing optical luminescent lifetime or phase shift optical sensing of oxygen which is relatively free of electrical interference; (2) allowing long term measurements of oxygen in various samples such as subsurface water samples; (3) enabling reliable measurements without requiring frequent calibrations; (4) including a protective oleophobic layer which can also be hydrophobic which protects an oxygen sensing layer of the oxygen sensor from hydrocarbons and/or organic solvents, thereby substantially increasing the useful life of the oxygen sensor.

FIG. 1 is a schematic block diagram of an oxygen sensing system 100 for optically sensing oxygen. The oxygen sensing system 100 includes an oxygen sensor 110, and a controller 140. A temperature sensor 130 can optionally be included in the oxygen sensing system 100. The oxygen sensing system 100 is configured to measure a concentration of oxygen in sample S such as, for example, a sub-surface water sample, a food sample, a bodily fluid (e.g., blood, urine, saliva, sweat, amniotic fluid, cerebrospinal fluid, etc.), a food sample, an agricultural sample, or any other sample described herein. The sample S can be a liquid or a gaseous sample. In some embodiments, the sample S can include aqueous samples contaminated with hydrocarbons (e.g., fossil fuel contaminated soil and ground water or fuel based organic solvents, for example, benzene, toluene, ethyl benzene, xylenes (BTEX), etc).

The oxygen sensor 110 includes a substrate 112, an oxygen sensing layer 120, and a protective layer 128 disposed over the oxygen sensing layer 120. The substrate 112 is structured to communicate optical signals. In some embodiments, the substrate 112 can include a fiber optic cable, for example, a multi-modal waveguide structured to communicate optical signals. The substrate 112 is optically coupled to the controller 140. The substrate 112 is configured to receive a first optical signal from the controller 140 and communicate the first optical signal to the oxygen sensing layer 120. Furthermore, the substrate 112 is configured to receive a second optical signal from the oxygen sensing layer 120 and communicate the second optical signal to the controller 140 as described herein.

In some embodiments, the substrate 112 can include a fiber optic cable. In such embodiments, the substrate 112 includes a tip which is transparent to allow the optical signal to pass through. Furthermore, the substrate 112 can include a sidewall which has an index of refraction that allows internal reflection. In some embodiments, the substrate 112 can have a cladding which has an index of refraction which provides internal reflection of the optical signal. Thus, substantially all the optical signal communicated into the substrate 112 (e.g., a fiber optic cable) is transmitted through the substrate 112 to the tip of the substrate 112. In some embodiments, the cladding or coating can be opaque.

In other embodiments, the substrate 112 can include a planar substrate, for example, a glass slide, a disc, a film or a glass sheet on which the oxygen sensing layer 120 is disposed. The planar substrate can also be contoured, for example, a glass lens. In such embodiments, the controller 140 or otherwise detectors included in the controller 140 can be disposed adjacent or otherwise proximal to the oxygen sensing layer 120. In still other embodiments, the substrate 112 can be a combination of a fiber optic cable and a planar substrate. For example, the substrate 112 can include a fiber optic cable that communicates the first optical signal to a planar substrate (e.g., a glass slide or a lens) via a suitable optical coupler.

The oxygen sensing layer 120 is disposed on the substrate 112. For example, the oxygen sensing layer 120 can be disposed on the tip of the substrate 112 such that the first optical signal can be communicated through the tip of the substrate 112 to the oxygen sensing layer 120. The oxygen sensing layer 120 includes an oxygen sensing molecule disposed or otherwise entrapped in a matrix. The oxygen sensing molecule is formulated to be in a first unexcited state. Furthermore, the oxygen sensing molecule is formulated to: (a) be excited in response to the first optical signal to move into a second state; (b) be quenched in the second state by oxygen present in the sample S in contact with the oxygen sensor 110; and (c) emit the second optical signal different from the first optical signal. An optical parameter of the second optical signal corresponds to an amount of oxygen present in the sample S.

Expanding further, the controller 140 generates the first optical signal which has a first optical parameter. The first optical parameter can include a first phase, a first optical intensity, a wavelength, a frequency, or any other suitable optical parameter which is configured to excite the oxygen sensing molecule to the second state. The oxygen in the sample S diffuses into the matrix of the oxygen sensing layer 120 within which the oxygen sensing molecule is suspended, dissolved or otherwise mixed. The oxygen quenches the excitation of the oxygen sensing molecule in the second state. The amount of quenching is directly proportional to the amount of oxygen present in the sample S. In particular embodiments, the oxygen sensing is performed once the oxygen in the sample S has reached steady state diffusion with the oxygen sensing layer 120 (i.e., flux of oxygen from the sample into the oxygen sensing layer 120 does not change with time).

The oxygen sensing molecule then returns to the first state and emits the second optical signal having an optical parameter (hereinafter "second optical parameter") which is different from the first optical parameter. The second optical parameter can correspond to a concentration of the oxygen present in the sample S. For example, the second optical parameter can include a phase which is different from a phase of the first optical signal. In other words, the second optical signal can be phase shifted from the first optical signal. The phase shift corresponds to the amount of quenching of the oxygen sensing molecule and thereby, the concentration of the oxygen in the sample S.

In other embodiments, the second optical parameter can be a luminescent lifetime of the oxygen sensing molecule. Expanding further, the amount of time it takes for the oxygen sensing molecule to be excited to the second state by the first optical signal and then return to the first state to emit the second optical signal is the luminescent lifetime of the oxygen sensing molecule. The oxygen sensing molecule can have a first luminescent lifetime in the absence of oxygen in which there is no quenching of the oxygen sensing molecule. The oxygen sensing molecule can thus experience maximum excitation before returning to the first state and emitting the second optical signal. In the presence of oxygen, the excitation of the oxygen sensing molecule is quenched such that the oxygen sensing molecule returns from the second state to the first state in a shorter period of time. Thus, the quenching urges the oxygen sensing molecule to have a second luminescent lifetime which is shorter than the first luminescent lifetime. The higher the amount of oxygen in the sample S, the shorter the second luminescent lifetime. In this manner, the difference between the first luminescent lifetime and the second luminescent lifetime can be correlated to the amount of oxygen present in the sample S.

For example, the oxygen-sensitive luminophore, platinum porphyrin (PtP) when subjected to a modulated excitation source, such as that of a pulsed light source, enters a singlet excited state, $^1S_1$. From here, the luminophore may lose energy either through luminescent or non-radiative decay, or undergo an intersystem crossing process and enter a triplet excited state ($^3T_1$). For PtP, $^3T_1$ yields are very high (approximately 100%) due to strong spin-orbit coupling induced by the presence of the heavy platinum atom. The triplet excited state then decays by either emitting photons, transferring the energy to molecular oxygen, or non-radiatively as heat. Since the emission of photons involves an electron spin flip to relax to the singlet ground state, $^1S_o$, the process is differentiated from luminescence where no spin flip is necessary. Here, the emission is known as phosphorescence, and can occur over timescales on the order of microseconds to seconds. The phosphorescence ideally follows an exponential decay of the form;

$$I=I_o e^{-t/\tau}+D_o$$

where $I_o$ represents the initial intensity of luminophore upon excitation, t is time, $\tau$ is the lifetime (duration) of the phosphorescence and $D_o$ is the background signal.

However, competing with phosphorescence is collision quenching by molecular oxygen. The two processes are inversely proportional—lower concentrations of surrounding oxygen leads to more phosphorescence and longer phosphorescence lifetimes, and vice versa. Quantitatively determining the lifetime can be directly related to the oxygen concentration.

In some embodiments, the oxygen sensing molecule can include an oxygen sensitive dye. Such dyes can include, for example, platinum meso-tetra(pentafluorophenyl)porphine, palladium meso-tetra(pentafluorophenyl)porphine, gadolinium meso-tetra(pentafluorophenyl)porphine, platinum octaethylporphine, palladium octaethylporphine, gadolinium octaethylporphine, platinum meso-tetraphenylporphine, platinum tetra(pentafluorophenyl)porpholactone, palladium meso-tetraphenylporphine, gadolinium meso-tetraphenylporphine, ruthenium tris(4,7-diphenyl-1,1.phenanthroline)Cl$_2$, osmium tris(bathophenanthroline) dichloride, iridium(III) bis(4-phenylthieno[3,2-c] pyridinato-N,C2')acetylacetonate, any other suitable oxygen sensitive dye or a combination thereof.

In some embodiments, the matrix within which the oxygen sensing molecule is disposed to form the oxygen sensing layer 120 can include a sol-gel. In particular embodiments, the sol-gel can include completely hydrolysable silanes (i.e., non-functional silane) and/or a linear alkyl silane (i.e., linear functional silane). For example, the inorganic silane can include tetraethoxysilane and the functionalized silane can include n-octyltriethoxysilane (C8-TEOS). In other embodiments, the inorganic silane can include tetraethylsilane and tetramethylsilane. In yet other embodiments, the functionalized silane can include n-octyltrichlorosilane and n-octyltrimethoxysilane.

The oxygen sensing molecule can be mixed with sol-gel precursors (i.e., monomers of the inorganic silane and/or functionalized silane) to form a solution, suspension or otherwise mixture which is disposed on the substrate 112. For example, the solution, suspension or otherwise mixture can be disposed using any suitable technique such as dip coating, drop coating, spin coating, vapor deposition, spray coating, or any other suitable technique. The solution, suspension or otherwise mixture can then be cured (e.g., air dried, vacuum dried, heated and/or a combination thereof) to remove any solvent to form the sol-gel matrix with the oxygen sensing molecule dispersed therein to form the oxygen sensing layer 120. The oxygen sensing layer 120 thus formed is physically and/or chemically robust and optically stable.

In other embodiments, the matrix can include a polymer matrix. The polymer matrix can be used in place of the sol-gel matrix to form the oxygen sensing layer 120 on the tip of the substrate 112. The polymer matrix can allow oxygen to diffuse through the matrix such that the oxygen can interact with the oxygen sensing molecule dispersed throughout the polymer matrix. Suitable polymers which can be used to form the polymer matrix can include poly vinyl chloride (PVC), poly(methyl methacrylate), polystyrene and derivatives, poly(vinyl acetate), fluorinated acrylics, polyurethane, any other suitable polymer or a combination thereof or any suitable matrix material.

Oxygen sensitivity can be dependent on the sol-gel or polymer used, and/or the thickness of the sol-gel polymer or otherwise matrix material used. Different sol-gels or polymers can elicit different response characteristics. Thus, the sensitivity of the oxygen sensing layer 120 for detecting a certain oxygen level can be tuned by choosing a sol-gel or polymer that has certain oxygen diffusion characteristics and matching it to a particular oxygen sensing molecule, with a lifetime appropriate for the application. Furthermore, a thickness of the sol-gel or polymer may be tuned so as to provide maximum diffusion of oxygen therethrough while maintaining sufficient quantity of the oxygen sensing molecule therein and minimize leaching of the oxygen sensing molecule therefrom. The polymer matrix including the oxygen sensing molecule can be disposed on the substrate 112 in a similar fashion to the sol-gel matrix and then cured (e.g., air dried, vacuum dried or heated) to form the oxygen sensing layer 120.

In some embodiments, the matrix can include a fluoropolymer within which the oxygen sensing molecule is dispersed. In one embodiment, the fluoropolymer can include a sulfonated tetrafluoroethylene fluoropolymer such as NAFION® which has a high resistance for dissolution against organic solvents. In another embodiment, the fluoropolymer can include the amorphous fluoropolymer CYTOP® available from Bellex International Corporation.

In some embodiments, the oxygen sensing molecule can be covalently linked to the surface of the substrate 112 using a linker to prevent leaching to the environment. In such embodiments, ionic or covalent bonding between the oxygen sensing molecule and the surface of the substrate (e.g., a glass optical fiber) can be used to produce a robust and stable oxygen sensor. In particular embodiments, bonding between the oxygen sensing molecule and the substrate 112 can be achieved using amine functional silane "adhesion promoters" or otherwise linkers. Such linkers generally consist of a silane reagent at one end, which bonds to a silicate (e.g., glass) surface, and an alkyl or functionalized alkyl side chain.

In other embodiments, the oxygen sensing molecule can be covalently linked to the matrix, for example, the sol-gel matrix or the polymer matrix. For example, functional groups on the periphery of oxygen sensing molecule (e.g., porphyrins) can enable covalent or ionic bonding of the oxygen sensing molecule to the matrix polymer. Covalent bonds can be prepared in the reaction of a functional porphyrin compound with a functional polymer. One example includes formation of an amide bond in the reaction of a carboxylic acid functional oxygen sensitive dye with amine functional polystyrene poly(4-aminostyrene). An esterification reaction bonds a carboxylic acid functional oxygen sensing molecule to a hydroxyl functional polyurethane which can be the polymer matrix.

In some embodiments, additives can also be disposed in the oxygen sensing layer 120 to improve the sensitivity and performance of the oxygen sensor 110. In particular embodiments, the additives can include photo-stabilizers. Such photo-stabilizers can include oxygen scavengers (e.g., singlet, doublet or triplet oxygen scavengers). The photo-stabilizers are formulated to remove residual oxygen molecules and/or radicals from the oxygen sensing layer 120 which can cause photo bleaching and degrade the performance of the oxygen sensing layer 120. Suitable photo-stabilizers can include, for example, nickel dibutyl dithiocarbamate and alpha-tocopherol.

The protective layer 128 is disposed on the oxygen sensing layer 120. The protective layer 128 is formed by disposing a membrane solution on the oxygen sensing layer 120 and allowing the membrane solution to cross-link or otherwise dry over the oxygen sensing layer to form the protective layer 128. The protective layer 128 is formulated to be oleophobic and can, furthermore be hydrophobic. Furthermore, the protective layer 128 allows oxygen to diffuse through to the oxygen sensing layer 120 and to protect the oxygen sensing layer 120 from hydrocarbons and organic solvents, as described herein. The oxygen sensor 110 can therefore, be used for sensing oxygen in samples (e.g., the sample S) that are contaminated with hydrocarbons or organic solvents, for example, sub surface water samples or soil samples.

In some embodiments, the protective layer 128 can include an amorphous fluoropolymer such as, for example, AF1600® (a copolymer of 2,2-bistrifluoromethyl-4,5-difluoro-1,3-dioxole and tetrafluoroethylene) available from DUPONT®, a fluoroacrylic copolymer (FIB) 1H,1H-dihydroperfluorobutyl methacrylate and 1,1,1,6,6,6-hexafluoroisopropyl methacrylate. The AF1600® can be dissolved in a solvent (e.g., Perfluoro-(2-perfluoro-n-butyl)tetrahydrofuran) or FIB can be dissolved in another solvent (e.g., α,α,α-trifluorotoluene) to form the membrane solution. The membrane solution is deposited on the oxygen sensing layer 120 and at least a portion of the substrate 112 such that the solution overcoats the oxygen sensing layer 120. The amorphous fluoropolymer membrane solution can then be cured (e.g., air dried, vacuum dried or heated) to remove the solvent. The fluoropolymer cross-links during the curing to form the protective layer 128 over the oxygen sensing layer 120.

In other embodiments, the protective layer 128 can include a long chain fluorinated alkyl silane. In some embodiments, the long chain fluorinated alkyl silane can include (Heptadecafluoro-1,1,2,2-tetra-hydrodecyl)triethoxysilane (FS) which is also sufficiently oleophobic and hydrophobic to form the protective layer. A membrane solution of the FS can be prepared in an appropriate solvent (e.g., isopropyl alcohol). The FS membrane solution is allowed to gel for a predetermined amount of the time. The gelled solution is over coated on the oxygen sensing layer 120 and at least a portion of the substrate 112, and cured to form the protective layer 128. Other long chain fluorinated alkyl silanes that can be used include (heptadecafluoro-1,1,2,2-tetrahydrodecyl)trichlorosilane, (heptadecafluoro-1,1,2,2-tetrahydrodecyl)trimethoxysilane. Other precursors that can be used include (tridecafluoro-1,1,2,2-tetrahydrooctyl) trichlorosilane, (tridecafluoro-1,1,2,2-tetrahydrooctyl) trimethoxysilane, and (tridecafluoro-1,1,2,2-tetrahydrooctyl)triethoxysilane.

In some embodiments, the protective layer 128 can include a TEFLON® membrane disposed over the oxygen sensing layer 120. The TEFLON® membrane can protect the oxygen sensing molecule from leaching from the oxygen sensing layer 120 into the sample S which contains hydrocarbons or organic solvents (e.g., fuel based organic solvents). Furthermore, the TEFLON® membrane also protects the oxygen sensing layer 120 from the hydrocarbons contaminating the sample S. A TEFLON® membrane has a high diffusion constant for oxygen and is inert to organic liquids. In one embodiment, the oxygen sensor can be prepared by disposing a first TEFLON® membrane coated with the oxygen sensing molecule at the tip of the substrate 112. The first TEFLON® membrane can be made by spin coating the oxygen sensing layer 110 solution onto stretched TEFLON® sheets. A second plain TEFLON® membrane is stretched over the first TEFLON® membrane to help secure it in place. The second TEFLON® membrane provides additional physical durability and acts as a barrier for contact with hydrocarbons and organic solvents. The first and second TEFLON® membranes can be fixed in place, for example, by adhesives, hot fusion bonding, solvent bonding, crimping, using a cap with a slide/lens sensing window, or heat shrink tubing.

In some embodiments, additives can also be included in the protective layer 128 to enhance one or more optical properties of the oxygen sensor 110 and/or improve the hydrophobicity and/or oleophobicity of the protective layer 128. In one embodiment, the additive can include one or more optical isolators such as, for example, titanium dioxide particles, carbon particles (e.g., bucky balls, carbon nanotubes, etc.), silicon dioxide particles, aluminum oxide particles, zinc oxide particles, zirconium dioxide particles, hollow glass spheres, any other optical isolators or a combination thereof. Such optical isolators can enhance optical performance of the oxygen sensor 110, for example, increase luminescent intensity of the oxygen sensing molecule. In other embodiments, the additives can include silver and/or copper ions to provide biofouling resistance. In still other embodiments, the additives can include silica and/or polymer particles to provide mechanical durability to the oxygen sensing layer 120.

In some embodiments, the oxygen sensing system 100 can also include a temperature sensor 130 electrically coupled to the controller 140. The temperature sensor 130 can include a probe type temperature sensor, for example, a thermocouple, a thermistor, or an optical temperature probe. For example, the temperature sensor can include an optical temperature sensor configured to measure temperature using a temperature sensitive luminescent dye. The temperature sensor 130 can be disposed in close proximity of the oxygen sensor 110 to measure a temperature of the sample S proximate to the oxygen sensor 110.

The temperature measurements can be correlated to the optical parameter of the second optical signal emitted by the oxygen sensing molecule to determine the amount of oxygen in the sample S. For example, the optical parameter of the second optical signal can be dependent not only on the amount of oxygen in the sample S but also on the temperature of the sample S. Thus the temperature data can be used to normalize a calibration curve of the optical parameter of the second optical signal to accurately determine the amount of oxygen in the sample S.

In some embodiments, the oxygen sensing system 100 can also include a pressure sensor (e.g., a barometer) to determine ambient air pressure. Since the partial pressure of oxygen in the sample S (e.g., an aqueous solution) can greatly vary with atmospheric pressure, the oxygen measurements can also be affected by ambient temperature measurements. The pressure measurement can be used to normalize the oxygen sensor measurements such that the oxygen concentration is determined with high accuracy.

In some embodiments, each of the oxygen sensor 110 and the temperature sensor 130 can be disposed in a sensor housing (not shown). The housing can be formed from a strong, rigid and/or corrosion resistance material, for example, stainless steel, aluminum, copper, titanium, any other metals or alloys, plastics, polymers, etc. and can define an internal volume within which the oxygen sensor 110 and the temperature sensor 130 can be disposed. The housing can prevent the oxygen sensor 110 and the temperature sensor 130 from physical damage while allowing the sample S to diffuse or otherwise be communicated into the internal volume of the housing to contact the oxygen sensor 110 and the temperature sensor 130. In some embodiments, the housing can also include wipers, brushes or a vibration mechanism, configured to periodically clean a surface of the sensors to ensure that fouling does not affect measurements.

The controller 140 is optically coupled to the substrate 112 and thereby, to the oxygen sensor 120. The controller 140 is structured to generate the first optical signal and communicate the first optical signal to the oxygen sensing layer 120 via the substrate 112. Furthermore, the controller 140 is structured to receive the second optical signal via the substrate 112 and analyze the optical parameter of the second optical signal to determine a concentration of the oxygen in the sample S.

The controller 140 can include a light source configured to generate the first optical signal. Any suitable light source can be used such as, for example, a light emitting diode (LED), a lamp, or a laser configured to produce the first optical signal. The first optical signal can have optical parameters such as, for example, phase, wave length and/or frequency suitable for exciting the optical sensing molecule from the first state to the second state. In particular embodiments, the light source can be an ultraviolet spectral range light source.

A light sensor can also be included in the controller 140. The light sensor can be configured to sense the second optical signal and determine the optical parameter of the second optical signal. For example, the controller 140 can include a spectrometer that includes the light source and the light sensor and/or detectors to sense the second optical signal.

The controller 140 can also include a processor configured to execute instructions stored on a computer readable medium to determine the concentration of the oxygen in the sample S from the second optical signal. For example, the controller 140 can be configured to compare the optical parameter of the second optical signal with calibration measurements (e.g., a calibration curve) stored on the computer readable medium to determine the concentration of oxygen in the sample S.

In some embodiments, the controller 140 can be configured to receive temperature data from the temperature sensor 130. Furthermore, the controller 140 can also be configured to receive pressure data from the pressure sensor or input manually by a user. In such embodiments, the calibration measurements on the computer readable medium can be temperature and/or pressure dependent. The controller 140 can be configured to correlate the temperature and/or pressure data to correlate the optical parameter of the second optical signal to a corresponding calibration curve or normalize the optical parameter of the second optical signal. In this manner, highly accurate measurement of the amount of oxygen in the sample S can be performed independent of the ambient temperature, pressure and/or the temperature of the sample S.

The processor can include a programmable logic chip (PLC), an ASIC chip, or a microcontroller configured to execute the instructions on the computer readable medium (e.g., a ROM, a RAM, a magnetic drive, a solid state drive, etc.). In one embodiment, the controller 140 can include a laptop, a desktop or a tablet computer programmed for determining the amount of oxygen from the optical parameter of the second optical signal. Moreover, the controller 140 can include a display to indicate to a user the measured concentration of oxygen in the sample S.

In some embodiments, the controller 140 can be in communication with a plurality of oxygen sensors and configured to receive optical signals from each of the oxygen sensors. The plurality of oxygen sensors can be in contact with multiple samples (e.g., a plurality of subsurface water wells). The controller 140 can be optically coupled to each sensor or configured to receive electrical signals corresponding to a second optical signal of each oxygen sensor via wired or wireless communication. In other words, the controller 140 can be networked with the plurality of oxygen sensors. The controller 140 can be thus be configured to determine the oxygen concentration of the multiple samples which can, for example, be used to determine an oxygen concentration landscape over a large area.

In particular embodiments, the controller 140 can also be configured to execute instructions programmed in a software stored on a computer readable medium. In such embodiments, the controller 140 can be configured to perform data management of one or multiple sensors, perform compliance reporting and determine if the one or more oxygen sensors are malfunctioning to perform troubleshooting.

Figure 2:
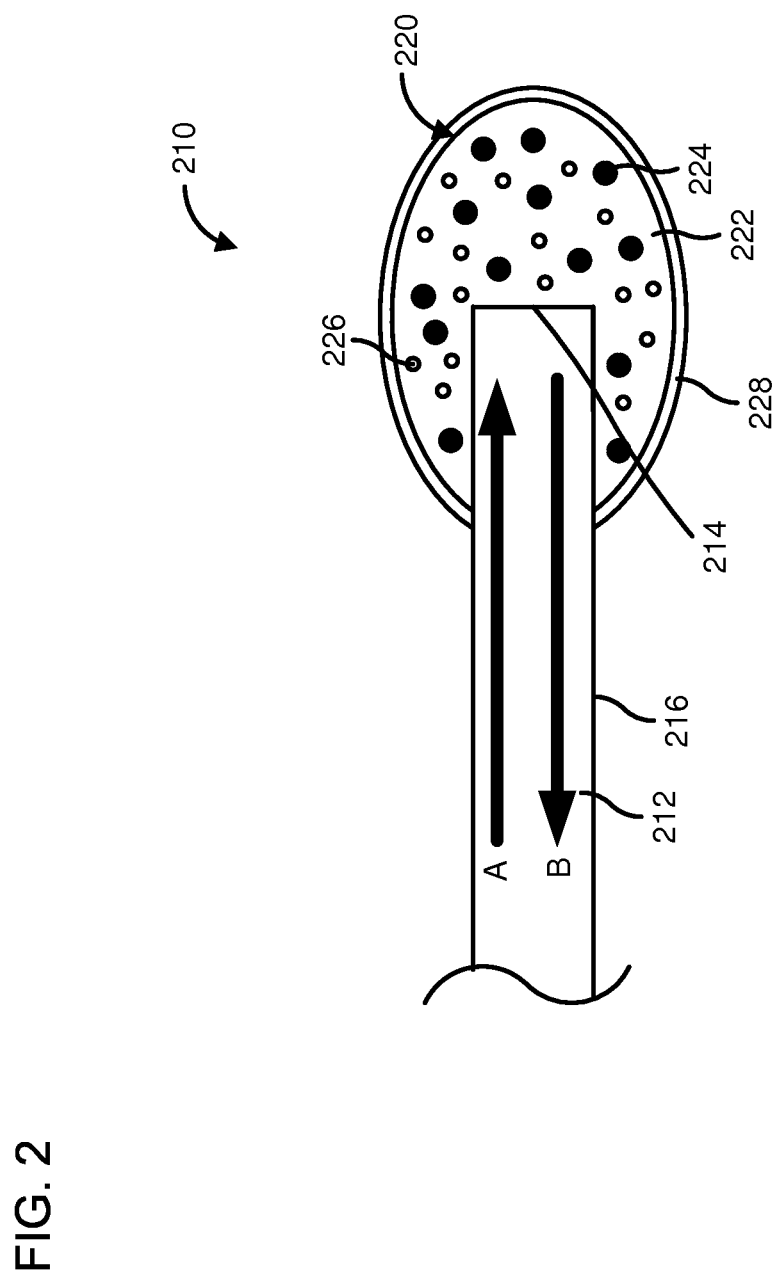
FIG. 2 is a schematic illustration of one embodiment of an oxygen sensor that includes an oxygen sensing layer disposed on a substrate and over coated with a protective layer.

FIG. 2 shows a schematic illustration of an oxygen sensor 210. The oxygen sensor 210 can be included in an oxygen sensing system, for example, the oxygen sensing system 100 or any other oxygen sensing system described herein. The oxygen sensor 210 includes a substrate 212, an oxygen sensing layer 220, and a protective layer 228. The oxygen sensor 210 can be used to measure the amount of oxygen in liquid or gaseous sample, for example, the sample S as described herein. The oxygen sensor 220 can be optically coupled to a controller (e.g., the controller 140) which is configured to determine the amount of oxygen in the sample based on an optical signal generated by the oxygen sensor 210.

The substrate 212 includes a fiber optic cable, for example, a multi-modal waveguide structured to communicate optical signals. The substrate 212 is configured to receive a first optical signal from a controller (e.g., the controller 140) and communicate the first optical signal to the oxygen sensing layer 220 in a direction shown by the arrow A. Furthermore, the substrate 212 is configured to receive a second optical signal from the oxygen sensing layer 220 and communicate the second optical signal to the controller in a direction shown by the arrow B.

A tip 214 of the substrate 212 is substantially transparent to allow the first optical signal A and the second optical signal B to pass through. A sidewall 216 of the substrate 212 is opaque, for example, coated with an opaque coating. The sidewall 216 prevents the optical signals from passing through the sidewall 216. Thus, substantially all of the optical signal communicated into the substrate 212 is communicated through the substrate 212 to the tip 214 of the substrate 212, or otherwise from the tip 214 to the controller.

The oxygen sensing layer 220 is disposed on and around the tip 214 of the substrate 212. In this manner, the first optical signal A is communicated through the tip 214 of the substrate 212 to the oxygen sensing layer 220. In other embodiments, the oxygen sensing layer 220 can be coated on a sidewall 216 of the substrate 212. In such embodiments, an evanescent field of the first optical signal can interact with the oxygen sensing layer 220 along the sidewall 216 of the substrate 212 and excites the oxygen sensing molecule 224 disposed within the oxygen sensing layer 220. In still other embodiments, a bifurcated patch cord can be used to optically couple the substrate 212 (e.g., the fiber optic cable) to the controller. The bifurcated patch cord includes a "Y" shaped cord or fiber optic cable that allows each of the excitation source which produces the first optical signal and a detector which receives and detects the second optical signal to be optically coupled to the substrate 212.

The oxygen sensing layer 220 includes an oxygen sensing molecule 224 disposed or otherwise entrapped in a matrix 222. The oxygen sensing molecule 224 is formulated to be in a first unexcited state. Furthermore, the oxygen sensing molecule 224 is formulated to: (a) be excited in response to the first optical signal A to move to a second state; (b) be quenched in the second state by oxygen present in a sample (e.g., the sample S) in contact with the oxygen sensor 220; and (c) emit the second optical signal B different from the first optical signal A, an optical parameter of the second optical signal B corresponding to an amount of oxygen present in the sample.

In some embodiments, the oxygen sensing molecule 224 can include an oxygen sensitive dye, for example a platinum prophyrin or any other oxygen sensitive dye as described with respect to the oxygen sensing molecule included in the oxygen sensing layer 120 of the oxygen sensor 110.

The matrix 222 includes a plurality of pores 226 to allow oxygen to diffuse through the matrix 222 and react with the oxygen sensing molecules 224. In other words, the matrix 222 is sufficiently porous to allow free or otherwise steady state diffusion of oxygen through the oxygen sensing layer 220. Furthermore, the pores 226 are sized to prevent the oxygen sensing molecule 224 from leaching from the matrix 222. In some embodiments, the matrix 222 can include a sol-gel. In particular embodiments, the sol-gel can include an inorganic silane (e.g., tetraethyl orthosilicate (TEOS)) and/or a functionalized silane (n-octyltriethoxy silane (C8-TEOS)), or any other sol-gel described herein.

The oxygen sensing molecule 224 can be mixed with sol-gel precursors (i.e., monomers of the inorganic silane and/or functionalized silane) to form a solution, suspension or otherwise mixture which is disposed on the substrate 212. For example, the solution, suspension or otherwise mixture can be disposed on the tip 214 of the substrate 212 using any suitable technique such as dip coating, drop coating, spin coating, vapor deposition, spray coating, or any other suitable technique. The solution, suspension or otherwise mixture can then be cured (e.g., air dried, vacuum dried, heated and/or a combination thereof) to remove any solvent to form the matrix 222 (i.e., a sol-gel matrix) with the oxygen sensing molecule 224 dispersed therein to form the oxygen sensing layer 220.

In other embodiments, the matrix 222 can include a polymer matrix, as described with respect to the matrix included in the oxygen sensing layer 120 of the oxygen sensor 110. Suitable polymers which can be used to form the matrix 222 can include poly vinyl chloride (PVC), poly (methyl methacrylate), polystyrene and derivatives, poly (vinyl acetate), fluorinated acrylics, polyurethane, any other suitable polymer or a combination thereof. The polymer matrix including the oxygen sensing molecule 224 can be disposed on the substrate 212 in a similar fashion as the sol-gel matrix and then cured (e.g., air dried, vacuum dried or heated) to form the oxygen sensing layer 220.

In some embodiments, the matrix 222 can include a fluoropolymer within which the oxygen sensing molecule 220 is dispersed. In one embodiment, the fluoropolymer can include a sulfonated tetrafluoroethylene fluoropolymer such as NAFION® which has a high resistance for dissolution against organic solvents. In another embodiment, the fluoropolymer can include the amorphous fluoropolymer CYTOP® available from Bellex International Corporation.

In other embodiments, the oxygen sensing molecule 224 can be covalently linked to the matrix 222. For example, functional groups on the periphery of the oxygen sensing molecule 224 (e.g., porphyrins) can enable covalent or ionic bonding of the oxygen sensing molecule 224 to the matrix 222 polymer. Covalent bonds can be prepared in the reaction of a functional porphyrin compound with a functional polymer. One example includes formation of an amide bond in the reaction of a carboxylic acid functional oxygen sensitive dye with amine functional polystyrene poly(4-aminostyrene). An esterification reaction bonds a carboxylic acid functional oxygen sensing molecule 224 to a hydroxyl functional polyurethane which forms the polymer matrix 222.

In some embodiments, additives can also be disposed in the oxygen sensing layer 220 to improve the sensitivity and performance of the oxygen sensor 210. In particular embodiments, the additives can include photo-stabilizers. Such photo-stabilizers can include oxygen scavengers (e.g., singlet, doublet or triplet oxygen scavengers) as described with respect to the oxygen sensing layer 120 of the oxygen sensor 110.

The protective layer 228 is disposed on the oxygen sensing layer 220 and at least a portion of the sidewall 216 of the substrate 212 proximal to the tip 214. In other word, the protective layer 228 overcoats the oxygen sensing layer 210. The protective layer 228 can be formed by disposing a membrane solution on the oxygen sensing layer 220 and allowing the membrane solution to cross-link. The protective layer 228 is formulated to be oleophobic and can also be hydrophobic. Furthermore, the protective layer 228 allows oxygen to diffuse through to the oxygen sensing layer 220 while protecting the oxygen sensing layer 220 from hydrocarbons and organic solvents, as described herein. This allows the oxygen sensor 210 to be used for sensing oxygen in samples that are contaminated with hydrocarbons or organic solvents, for example, sub surface water samples.

In some embodiments, the protective layer 228 can include an amorphous fluoropolymer such as, for example, AF1600® available from DUPONT® or CYTOP® available from Bellex International Corporation. In other embodiments, the protective layer 228 can include a long chain fluorinated alkyl silane dissolved, suspended or otherwise mixed in a matrix, for example, a sol-gel matrix. In some embodiments, the long chain fluorinated alkyl silane can include (Heptadecafluoro-1,1,2,2-tetra-hydrodecyl)triethoxysilane (FOS) which is also sufficiently hydrophobic and oleophobic to form the protective layer 228. The amorphous polymer protective layer 228 or the long chain fluorinated alkyl silane protective layer 228 can be prepared and disposed on the oxygen sensing layer 220 substantially similar to the protective layer 128, and therefore not described in further detail herein.

In some embodiments, the protective layer 228 can include a TEFLON® membrane disposed over the oxygen sensing layer 220. The TEFLON® membrane can protect the oxygen sensing molecule 222 from leaching from the oxygen sensing layer 220 into the sample which contains hydrocarbons or organic solvents (e.g., fuel based organic solvents).

In some embodiments, additives can also be included in the protective layer 228 to enhance one or more optical properties of the oxygen sensor 210 and/or improve the hydrophobicity, oleophobicity and/or chemical durability (e.g., to prevent leaching or etching of the components of the oxygen sensing layer 220) of the protective layer 228. In one embodiment, the additive can include one or more optical isolators such as, for example, titanium dioxide, carbon, any other suitable optical isolators or a combination thereof as described before herein. Such optical isolators can enhance optical performance of the oxygen sensor 210, for example, increase luminescent intensity of the oxygen sensing molecule 222. In other embodiments, the additives can include silver and/or copper ions to provide biofouling resistance. In still other embodiments, the additives can include silica and/or polymer particles to provide mechanical durability to the oxygen sensing layer 120.

Figure 3:
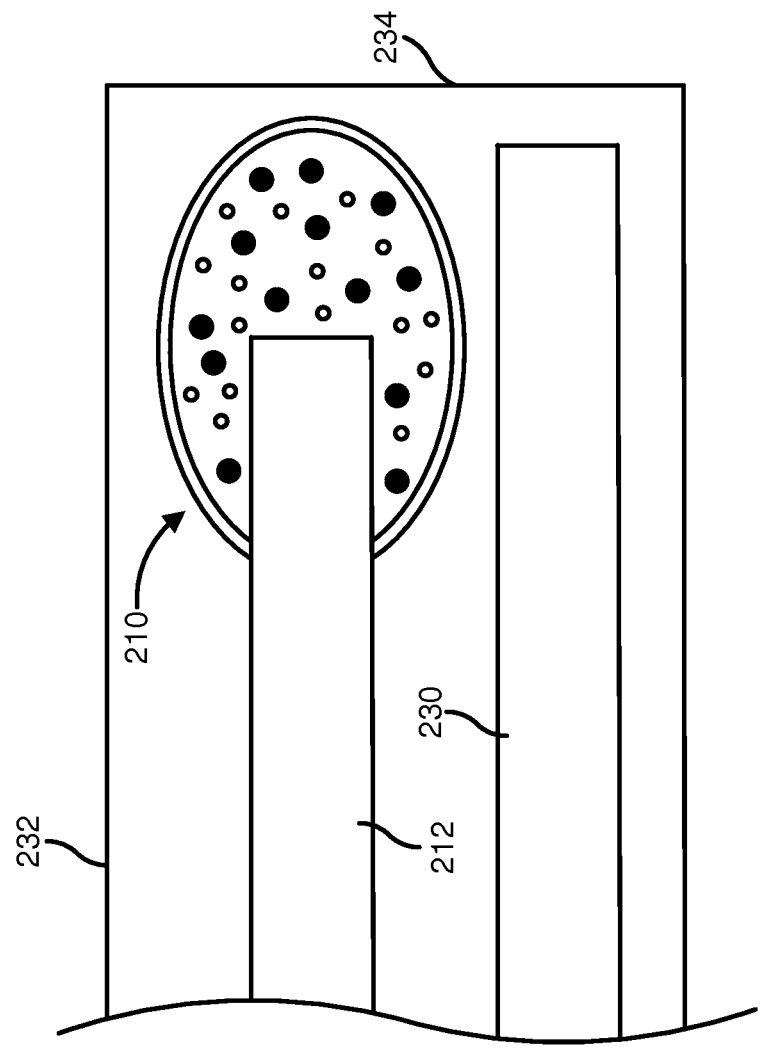
FIG. 3 is a schematic illustration of the oxygen sensor of FIG. 2 and a temperature sensor disposed in a housing which is configured to protect the oxygen sensor and the temperature sensor from physical damage.

In some embodiments, a temperature sensor can also be included with an oxygen sensor which can be disposed together in a housing. For example, FIG. 3 shows the oxygen sensing layer 210 and at least a portion of the substrate 212 included in the oxygen sensor 210 disposed in an internal volume defined by a housing 232. The housing 232 can be formed from a strong, rigid, and corrosion resistant materials. Suitable materials can include metals (e.g., stainless steel, aluminum, titanium, alloys, etc.), plastics, hard rubber, polymers, any other suitable material or a combination thereof.

At least a portion of the housing 232 can be porous or otherwise structured to allow a sample (e.g., the sample S) to diffuse or otherwise flow into the internal volume of the housing 232. For example, a sidewall 234 of the housing 232 can be porous, define an opening, or otherwise be removed to allow a gaseous or liquid sample (e.g., the sample S) to be communicated into the internal volume of the housing 232 and allow the sample to contact the oxygen sensor 210. The oxygen sensor 210 is recessed inside the housing 232 such that the oxygen sensor 210 is protected from physical damage which can occur due to physical contact while still being able to contact the sample. Furthermore, a structure and/or dimension of the housing 232 can be varied for different applications.

A temperature sensor 230 is also disposed in the housing 232 in close proximity to the oxygen sensor 210 to measure a temperature of the sample (e.g., the sample S). The temperature sensor 230 can include a probe type temperature sensor, for example, a thermocouple, a thermistor, or an optical temperature sensor. The temperature measurements can be correlated to the optical parameter of the second optical signal emitted by the oxygen sensing molecule 224 to determine the amount of oxygen in the sample. For example, the optical parameter of the second optical signal can be dependent not only on the concentration of oxygen in the sample but also on the temperature of the sample. Thus the temperature data can be used to normalize a calibration curve of the optical parameter of the emitted second optical signal to accurately determine the amount of oxygen in the sample.

Figure 4:
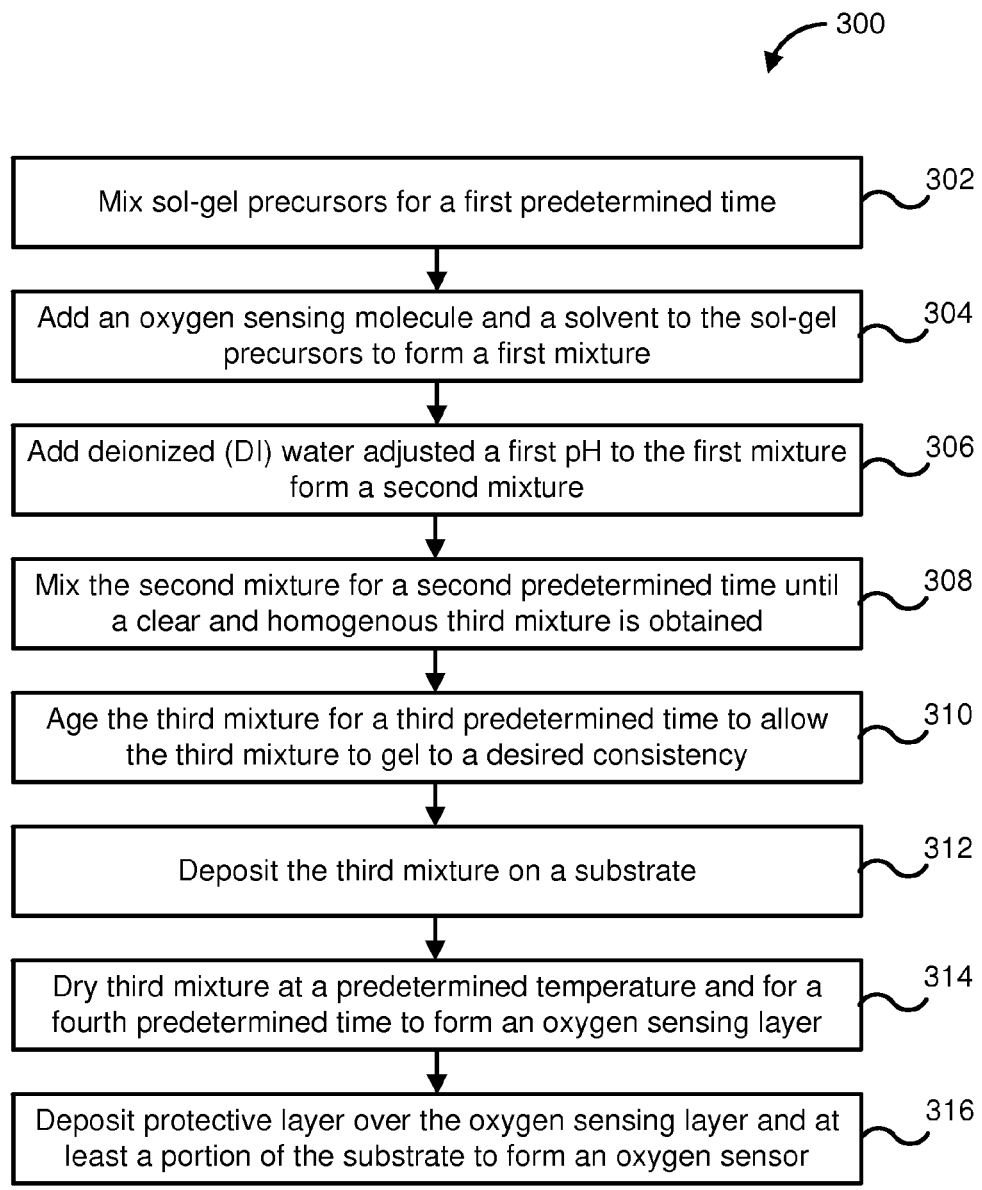
FIG. 4 is a schematic flow diagram of a method for preparing an oxygen sensor, according to one embodiment.

FIG. 4 shows a schematic flow diagram of an exemplary method 300 for preparing an oxygen sensor (e.g., the oxygen sensor 110, 210 or any other oxygen sensor described herein. The oxygen sensor thus formed can be used to measure oxygen in a gaseous or liquid sample, for example, the sample S or any other sample described herein.

The method 300 includes mixing sol-gel precursors for a first predetermined amount of time, at 302. In one embodiment, the precursors can include TEOS and C8-TEOS in a molar ratio of about 0.5:0.5. The sol-gel precursors can be mixed for about 5 minutes in an inert container such as a plastic container (e.g., polyethylene or poly propylene).

An oxygen sensing molecule (e.g., any oxygen sensing molecule as described with respect to the oxygen sensor 110 or 210) and a solvent are added to the sol-gel precursors to form a first mixture, at 304. In some embodiments, the amount of the oxygen sensing molecule can be approximately 0.5% by weight of a final dry weight of the sol-gel precursors, or about 0.007% by weight of total weight. Any suitable solvent can be used such as, for example, ethanol, isopropyl alcohol, methanol, acetone, etc. Moreover, a molar ratio of the solvent to the sol-gel precursors can be about 0.5:0.5:4. In some embodiments, a photo-stabilizer as described herein can also be added to first mixture at a predetermined ratio. The first mixture can be sonicated to ensure that the oxygen sensing molecule is uniformly dispersed in the first mixture and no clumps are formed.

A molar ratio of the precursors (e.g., TEOS and C8-TEOS) to the DI water can be about 0.5:0.5:4. Deionized (DI) water adjusted to a first pH is added to the sol-gel precursors to form a second mixture, at 306. In particular embodiments, the DI water can be adjusted to the first pH, for example, a pH of about 1 by adding HCl to the DI water and mixing. In some embodiments, a base can also be added to the DI water. The pH acts as a catalyst to promote the cross linking of the precursors. The catalyst promotes hydrolysis of the sol-gel which eventually leads to cross-linking and polymerization of the sol-gel. In other embodiments, the sol-gel precursors can be mixed with DI water at a neutral pH first to form a mixture, and then an acid can be added to mixture to achieve the desired pH, for example, a pH of about 1. In still other embodiments, a base as well as the acid can be added with the neutral pH.

The second mixture including the oxygen sensing molecule and solvent is then mixed (e.g., using a magnetic stirrer or sonicated) for a second predetermined time until a clear and homogenous third mixture is obtained, at 308. For example, the second mixture can be mixed for about 15-20 minutes until the clear and homogenous third mixture is obtained. The third mixture can be disposed in a plastic container which is capped during mixing. In some embodiments, each component i.e., DI water, acid (e.g., HCl), base, and the oxygen sensing molecule can be added together at the same time and mixed together to form the third mixture.

The third mixture is aged for a third predetermined time to allow the third mixture to obtain a desired consistency, at 310. The amount of gelling can determine the thickness of the oxygen sensing layer. The plastic container can be uncapped and allowed to sit for about 3 hours or any other suitable time until the third mixture starts to gel and a desired gel consistency is obtained.

The third mixture is deposited on a substrate, at 312. The substrate can include a fiber optic cable or any other substrate (e.g., the substrate 112 or 212) described herein. The third mixture can be disposed on the substrate using spin coating, spray coating, drop coating, dip coating, vapor deposition, or any other suitable method.

The third mixture is then dried at a predetermined temperature and for a fourth predetermined time to form an oxygen sensing layer, at 312. In particular embodiments, the third mixture can be air dried for at least about 24 hours. The third mixture can then be cured at 45 degrees Celsius for about 3 hours such that the oxygen sensing layer is formed on the substrate. The curing can be performed in any suitable heating setup, for example, an oven. The curing is performed by slow ramping of the temperature to prevent thermal stresses which can crack the oxygen sensing layer. The substrate with the third mixture disposed thereon can then be left in a dust free and dark environment for at least 5 days before use.

A protective layer is deposited over the oxygen sensing layer and at least a portion of the substrate to form an oxygen sensor, at 314. The protective layer is oleophobic and can also be hydrophobic, and is formulated to protect the oxygen sensing layer from hydrocarbons or organic solvents present in a sample. In some embodiments, the protective layer can include an amorphous fluoropolymer, for example, the amorphous fluoropolymer AF1600® from DUPONT®, which has hydrophobic and oleophobic properties. In such embodiments, a membrane solution of the protective layer can be formed by dissolving the amorphous fluoropolymer at a predetermined weight percentage (e.g., about 5% by weight) in a suitable solvent (e.g., α, α, α-trifluorotoluene).

In other embodiments, the protective layer can include a long chain fluorinated alkyl silane such as FS which is also hydrophobic and oleophobic. In such embodiments, the FS protective layer can be prepared by mixing FS precursor with DI water adjusted to a pH of about 1, and isopropyl stock solution at a ratio of about 1:4:4 for 15-20 minutes to form a membrane solution. The membrane solution can be allowed to sit for about 3 hours to allow the solution to gel to a desired consistency.

The protective layer is deposited over the oxygen sensing layer using any suitable method such as, for example, dip coating, drop coating, spray coating, spin coating, vapor deposition or any other suitable method. The protective layer over coats the oxygen sensing layer and is disposed on at least a portion of the substrate to prevent the hydrocarbons included in the sample from contacting any portion of the oxygen sensing layer. Furthermore, the oxygen sensing layer is sufficiently porous to allow the sample and/or the oxygen included in the sample to diffuse through the protective layer and react with the oxygen sensing molecule such that oxygen can be sensed. A plurality of coats of the protective layer can be disposed on the oxygen sensing layer to obtain a desired thickness and/or porosity of the protective layer. In particular embodiments, two coats of the protective layer can be deposited over the oxygen sensing layer with a 30 minute rest period between each coat.

In some embodiments, a protective layer can also include an anti-fouling layer configured to protect a sensing layer of an optical sensor (e.g., the oxygen sensing layer 120/220 or any other sensing layer) from fouling. Fouling as described herein relates to degradation in the performance of the optical sensors described herein due to deposition or otherwise growth thereon of organic and/or inorganic matter, bacterial biofilms, fungal colonies, for example when such sensors are immersed in fluids such as water. Fouling, for example biofouling can be a major source of sensor degradation in many applications including medical devices, marine vessels, water purification filters, pipelines and environmental sensors. Moreover, fouling in particular may be a central contributor in limiting the performance and/or operational lifetime of optical sensors used for water quality monitoring, for example dissolved oxygen sensors. In some embodiments, the protective layer can include an integrated protective layer configured to protect an oxygen sensing layer positioned therebeneath from hydrocarbons and organic solvents, as well as from fouling.

Figure 5:
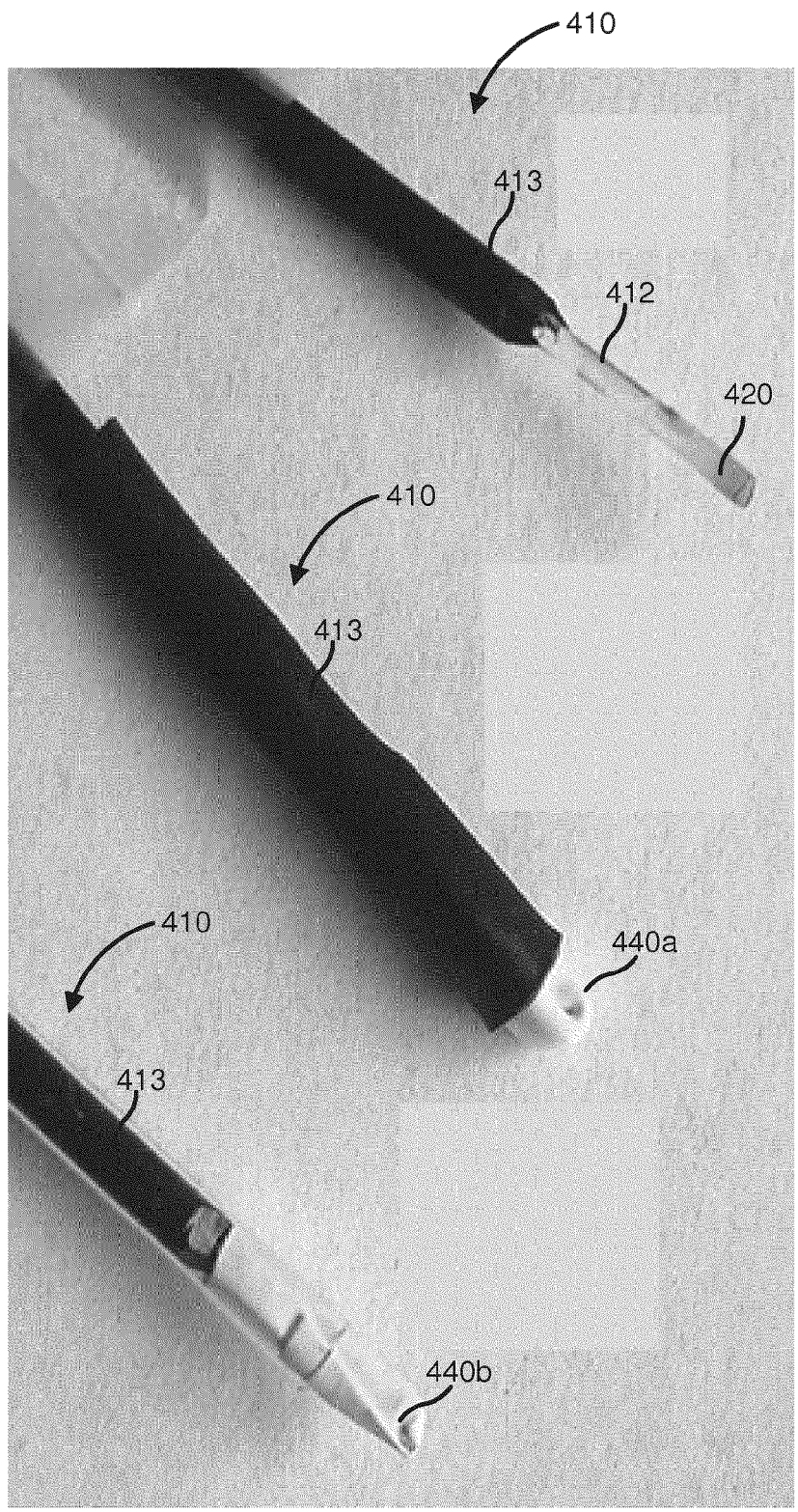
FIG. 5 are images of an embodiment of an optical fiber based optical sensor (top) which includes a sensing layer positioned on an end of a substrate of the sensor, and a portion of the optical fiber covered with a first anti-fouling layer (middle) and a second anti-fouling layer (bottom).

FIG. 5 includes optical images of an optical sensor 410 according to an embodiment. The optical sensor 410 includes a substrate 412 (FIG. 5, top). The substrate 412 can be substantially similar to the substrate 112, described before and therefore not described in further detail herein. A portion of the substrate 412 is coated with a cladding 413 so that a tip of the optical sensor 410 is exposed. The cladding 413 may have an index of refraction which provides internal reflection of an optical signal communicated through the substrate 410. Thus, substantially all the optical signal communicated into the substrate 412 (e.g., a fiber optic cable) is transmitted through the substrate 412 to the tip of the substrate 412. In some embodiments, the cladding 413 may be opaque.

An optical sensing layer 420 is disposed on the tip of the substrate 412. In some embodiments, the optical sensing layer 420 can include an oxygen sensing layer, for example the oxygen sensing layer 120/220 described before herein. In other embodiments, the optical sensing layer 420 can be configured to sense any other analyte, for example ions such as calcium, sodium, potassium, chlorine etc., a nitrogen or any other compound. In some embodiments, the optical sensing layer 420 can also be coated with an oleophobic protective layer (e.g., the oleophobic protective layer 128/228 described before herein).

FIG. 5 (middle) shows the tip of the optical sensor 410 coated with a first protective layer 440a and FIG. 5 (bottom) shows the tip of the optical sensor coated with a second protective layer 440b (collectively referred to herein as "the protective layers 440"). The first protective layer 440a is the same as the second protective layer 440b with the exception that the first protective layer 440a has a larger internal cross-section relative to the second protective layer 440b.

The protective layers 440 include a membrane that includes an anti-fouling compound to prevent biofouling while allowing the sample (e.g., water) and/or oxygen to diffuse through the optical sensing layer 420. For example, the protective layers 440 may include a polytetrafluoroethylene (PTFE) membrane that contains (e.g., is infused with) an antibacterial or anti-fungal agent (e.g., silver ions, cuprous oxide, antibiotics, antifungals, etc.) or any other anti-fouling agent formulated to prevent the deposition or otherwise formation of biofilms on the optical sensor 410.

In some embodiments, the anti-fouling agent can include N-alky poly (4-vinyl-pyridine) groups covalently bonded to the substrate 412 (e.g., a glass substrate) so as to form a protective layer around the optical sensing layer 420 (e.g., an oxygen sensing layer). Compounds including N-alky poly (4-vinyl-pyridine) groups can prevent biofouling due to gram-positive as well as gram-negative bacteria.

In some embodiments, the anti-fouling agent can include N-halomines which are a class of regenerating anti-microbial compounds. These compounds derive their anti-microbial properties by virtue of their covalent binding capacity for the halogens chlorine and bromine. In some embodiments, the protective layer 440 can include a bio-textile material, for example cotton, silk, rayon, wool, etc. coated or otherwise infused with carbohydrate based antibacterial agents. In some embodiments, the protective layer 440 may include an antibiotic containing polyester.

In some embodiments, the protective layers 440 can include an anti-fouling paint disposed (e.g., coated or otherwise deposited) over the optical sensing layer 420 (e.g., an oxygen sensing layer) of the optical sensor 410. The anti-fouling paint can include various paints used in the shipping industry that contain biocidal agents such as, for example cuprous oxide or silver, which are toxic to microorganisms when released at a controlled rate in fluids such as water.

In various embodiments, an optical sensor maybe positioned within a housing and surrounded by a plurality of fouling-resistant particles to protect the optical sensor from biofouling. For example, FIG. 6A is a side view and FIG. 6B is a side cross-section view of a housing 532 within which an optical sensor 510 is disposed. The optical sensor 510 includes a substrate 512 (e.g., fiber optic cable) at least a portion of which is covered by a cladding 513 such that a tip of the substrate 512 is exposed. The substrate 512 and the cladding 513 can be substantially similar to the substrate 412 and cladding 413, or any other substrate (e.g., the substrate 112/212) or cladding described herein and, therefore not described in further detail herein.

An optical sensing layer 520 is positioned on the tip of the substrate 512. The optical sensing layer 520 can include an oxygen sensing layer (e.g., the oxygen sensing 120/220) or any other oxygen sensing layer described herein. Furthermore, a protective layer 540 may be positioned on the tip of the substrate 512 so as to overcoat or otherwise surround the optical sensing layer 520. The protective layer 540 may include an oleophobic and/or hydrophobic membrane (e.g., the protective layer 128/228), an anti-fouling membrane (e.g., the protective layer 440) or any combination thereof.

The housing 532 defines an internal volume for housing at least a portion of the optical sensor 510 that includes the optical sensing layer 520. One or more openings 534, for example slits, holes, slots, pores, etc. are defined on at least one sidewall of the housing 534. The openings 534 may allow delivery of a sample, for example a fluid such as water therethrough into the internal volume, thereby allowing the sample to contact the optical sensing layer (e.g., an oxygen sensing layer). The housing 532 can have any suitable shape, for example round, elliptical, square, rectangular or polygonal. In some embodiments, the housing 532 can also be made from a biocidal material, for example copper or silver, or coated with a biocidal material (e.g., anti-fouling paint).

A plurality of fouling-resistant particles 536 are positioned within the internal volume of the housing 532 so that the internal volume is packed with the fouling-resistant particles 536. In some embodiments, the fouling-resistant particles 536 may include beads, for example glass beads or plastic beads coated with or infused with a biocidal agent. For example, the beads can include an antifouling agent, for example ionic silver or cuprous oxide encased in glass microparticles. The portion of the optical sensor 510 is positioned within the internal volume of the housing 532 such that the plurality of fouling-resistant particles 536 surround the portion of the optical sensor 510, thereby providing an fouling-resistant or anti-fouling barrier around the portion of optical sensor 510 (e.g., an oxygen sensor).

FIG. 6B shows the fouling-resistant particles 536 as having about the same size. In some embodiments, the internal volume of the housing 532 may be packed or otherwise filled with fouling-resistant particles 536 having various sizes and gradations so as to physically block the flow of silt, sand and/or organic matter entering the internal volume of the housing 532 via the openings 534, while allowing the liquid sample to flow to the optical sensing layer 520.

Figure 7:
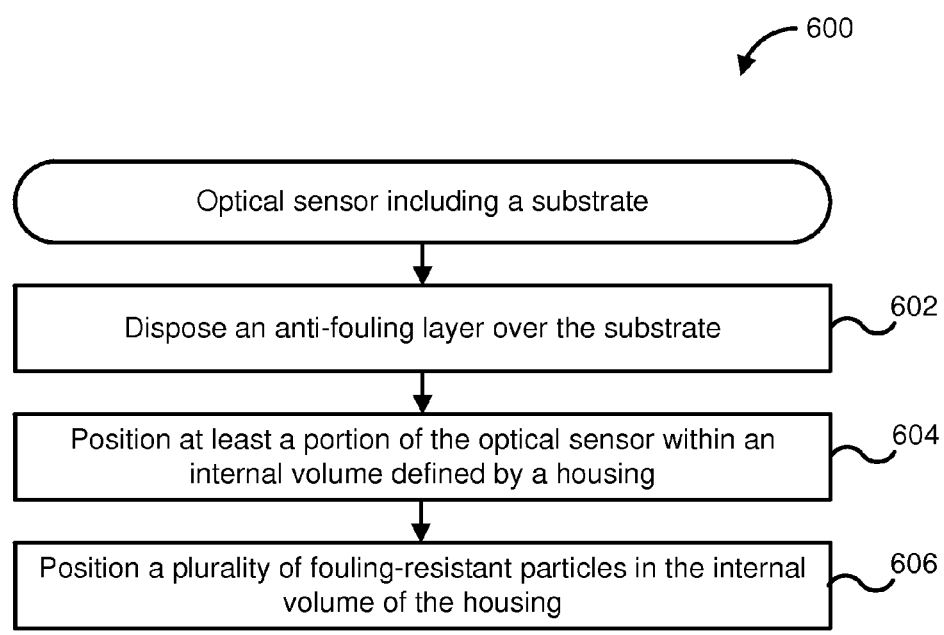
FIG. 7 is a schematic flow diagram of an embodiment of a method to prevent fouling of an optical sensor.

FIG. 7 is a schematic flow diagram of an example method 600 for protecting an optical sensor (e.g., the oxygen sensor 110/210 or the optical sensor 410/510) from fouling. The optical sensor includes a substrate (e.g., the substrate 112/212/412/512) at least a portion of which is coated with optical sensing layer (e.g., the oxygen sensing layer 120/220 or the optical sensing layer 420/520).

The method 600 includes disposing an anti-fouling layer over the substrate at 602. For example, the anti-fouling layer 440/540 may be disposed over the substrate 112/212/412/512 to overcoat the oxygen sensing layer 120/220 or the optical sensing layer 420/520 positioned on at least a portion of the substrate. In some embodiments, the anti-fouling layer may be disposed over an oleophobic and/or hydrophobic protective layer (e.g., the protective layer 128/228) positioned over the oxygen sensing layer 120/220 or the optical sensing layer 420/520. In some embodiments, the anti-fouling layer can also be configured to be oleophobic and/or hydrophobic so as to protect the oxygen sensing layer 120/220 or the optical sensing layer 420/520 from fouling as well as hydrocarbons and organic solvents.

At least a portion of the optical sensor is positioned within an internal volume defined by a housing at 604. For example, a portion of the optical sensor 110/210/410/510 including the oxygen sensing layer 120/220 or the optical sensing layer 420/520 is positioned within the housing 232/532. A plurality of fouling-resistant particles are positioned in the internal volume of the housing so as to surround the portion of the optical sensor positioned within the internal volume of the housing at 606. For example, the fouling-resistant particles 536 are disposed or packed inside the internal volume of the housing 232/532 so as to surround the portion of the optical sensor 110/210/410/510 positioned within the internal volume of the housing 532. As described before, fouling-resistant particles (e.g., microbeads coated or infused with biocidals) protect the optical sensing layer of the optical sensor from biofouling as well as fouling from organic or inorganic debris (e.g., silt, sand, debris, etc.)

Another component involved in reliable performance of sensors, and optical sensors in particular is calibration. Calibration protocols are generally chosen to address the key performance specifications, including detection range, detection limit, accuracy, response time, sensor drift, operational lifetime, etc. of optical sensors.

Generally, sensors such as the optical sensors described herein are calibrated in a controlled laboratory setting. For example, calibration may involve exposing the sensors to a set of samples having known concentrations of the target analyte to be sensed and recording the sensor response thereto. For example, the oxygen sensor 110/210 described herein may be calibrated by exposing the oxygen sensors 110/210 to water solutions containing known amounts of dissolved oxygen. The sensor response may be entered into an analytical function that describes the behavior of the optical oxygen sensor, for example temperature dependency, response time and/or drift characteristics.

However, in many instances laboratory calibration of the oxygen sensors described herein may not be possible. For example, the oxygen sensors described herein may be deployed at a remote location which is not readily accessible. Furthermore, the oxygen sensors described herein may be embedded within a permanent structure such that they cannot be easily removed therefrom for calibration.

In some embodiments, the oxygen sensors (e.g., the oxygen sensors 110/210 or any other oxygen sensors describe herein) may be calibrated in-situ by positioning a calibration device, for example a calibration probe proximate to the oxygen sensor. The calibration device may include a calibrant layer disposed on a substrate capable of communicating optical signals (e.g., a fiber optic cable). The calibrant layer may be responsive to optical signals to at least one of release a predetermined amount of heat, release a predetermined amount of oxygen or scavenge oxygen in proximity of the oxygen sensor so as to create an environment around the oxygen sensor having a predetermined temperature and/or oxygen concentration which may be used to calibrate the oxygen sensor (e.g., the oxygen sensor 110/210 or any other oxygen sensor described herein).

Figure 8:
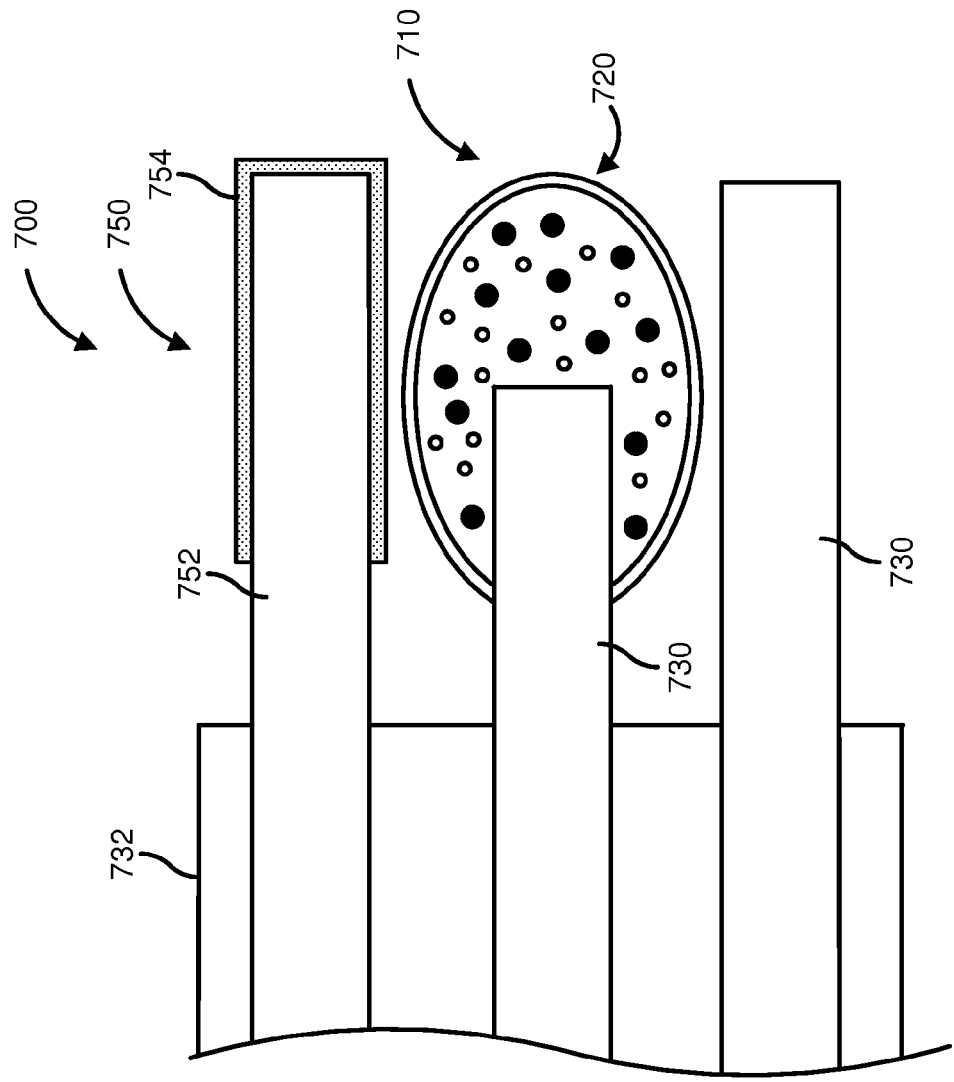
FIG. 8 is a schematic illustration of another embodiment of an oxygen sensing system which includes a calibration device configured to provide in-situ calibration of an oxygen sensor included in the oxygen sensing system.

For example, FIG. 8 is a schematic illustration of an oxygen sensor assembly 700 which includes an oxygen sensor 710, a calibration device 750, and optionally a temperature sensor 730. The oxygen sensor 710 includes a first substrate 712 and an oxygen sensing layer 720 positioned on at least a portion thereof (e.g., a tip of the first substrate 712). The oxygen sensor 710 and the temperature sensor 730 may be substantially similar to oxygen sensor 210 and the temperature sensor 230 and, therefore not described in further detail herein. At least a portion of the oxygen sensor 710, the temperature sensor 730 and the calibration device 750 may be permanently enclosed within a housing 732, for example a polyimide tubing. In some embodiments, a controller (e.g., the controller 170) may be communicatively coupled to each of the oxygen sensor 710, the temperature sensor 730 and the calibration device 750 and configured to control the operations thereof.

The calibration device 750 may include a second substrate 752 structured to communicate a calibrant optical signal (e.g., visible light or a laser pulse). The second substrate 752 may be substantially similar to the substrate 112/212 described before herein (e.g., include an optical fiber). A calibrant layer 754 is positioned on at least a portion of the second substrate 752, for example positioned at a location of the substrate 712 proximate to the oxygen sensor layer 720 of the oxygen sensor 710. The calibrant layer 754 is responsive to the calibrant optical signal to release a predetermined amount of heat, release a predetermined amount of oxygen and/or scavenge oxygen in proximity of the oxygen sensor 710 so as to create a predetermined temperature and/or oxygen environment around the oxygen sensor 720 for calibration thereof.

In some embodiment, the calibrant layer 754 may be formulated to release a predetermined amount of heat responsive to the calibrant optical signal. The response of the oxygen sensing layer 720 may be inherently dependent on the ambient temperature. Physical processes such as temperature dependent analyte permeability in the oxygen sensing layer 720 and thermal quenching of an oxygen sensing molecule included in the oxygen sensing layer 720 may cause variations in the oxygen response of the oxygen sensor 710.

Figure 9:
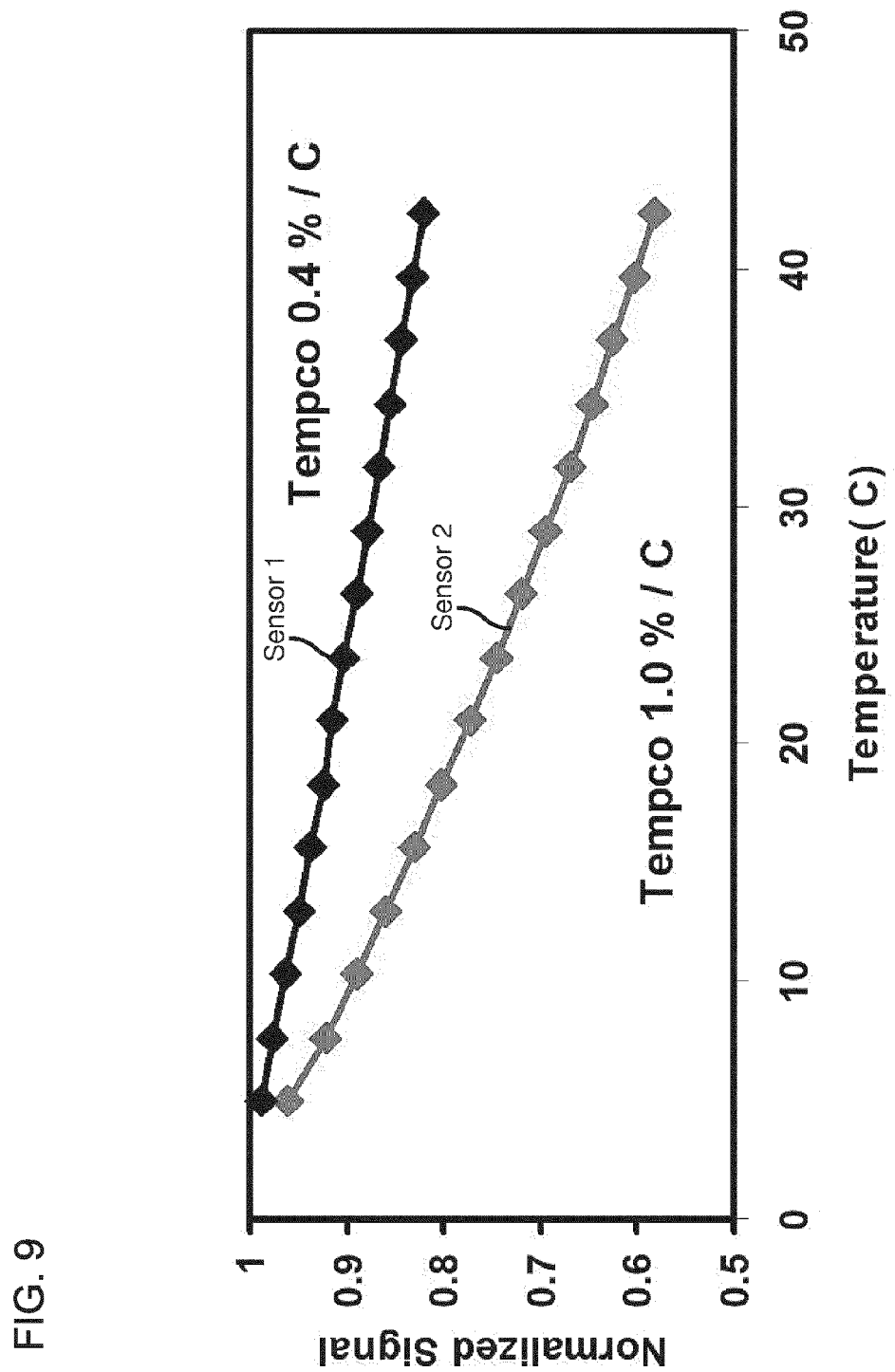
FIG. 9 is a plot of temperature dependence of a signal generated by two different oxygen sensors.

For example, FIG. 9 shows the response of a first oxygen sensor (sensor 1) and a second oxygen sensor (sensor 2). The first oxygen sensor includes a platinum porphyrin oxygen sensing dye embedded in a fluorinate acrylic matrix, and the second oxygen sensor includes the platinum porphyrin dye embedded in a polycarbonate matrix. Each of the first oxygen sensor and the second oxygen sensor demonstrate oxygen sensitive response. However, the second oxygen sensor demonstrates a larger degradation in the normalized signal in response to increasing temperature.

To calibrate the oxygen sensor to account for temperature changes, the controller (e.g., the controller 170) may generate a calibrant optical signal so as to urge the calibrant layer 754 to release the predetermined amount of heat so as to raise a temperature of the oxygen sensing layer to a predetermined temperature. For example, the calibrant layer 754 may include a highly absorbent non-luminescent chromophore. The calibrant optical signal (e.g., a laser signal) causes an increase in the temperature of the calibrant layer 754 so as to raise the temperature in the vicinity of the oxygen sensor 710 to a predetermined temperature (e.g., a 0.01 gram heat generating calibrant layer 754 which may have a specific heat of 1 J/C gram, may experience a temperature rise of about 10 degrees when exposed to a 100 mW laser for 1 second).

In some embodiments, the calibrant layer 754 may have a temperature dependence in the range of 0.25% oxygen per degree Celsius to 1.5% oxygen per degree Celsius. The controller (e.g., the controller 170) may determine a temperature dependency value of an optical parameter (e.g., an oxygen response signal) of the oxygen sensor 710 based on the predetermined temperature. The temperature dependency value may be compared to a known optical parameter value at the predetermined temperature so as to determine a temperature calibration value. The oxygen sensor 710 may be calibrated based on the temperature calibration value.

In some embodiments, the calibrant layer 754 may be formulated to release a predetermined amount of oxygen in response to the calibrant optical signal. For example, the calibrant layer may include an oxygen releasing molecule configured to release oxygen when exposed to heat or light. In some embodiments, the oxygen releasing molecule may include potassium peroxide which releases oxygen in a temperature dependent reaction as follows:

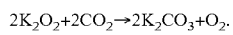

$$2K_2O_2+2CO_2 \rightarrow 2K_2CO_3+O_2.$$

The oxygen releasing molecule may be mixed in a hydrophilic polymer (e.g., polyethylene glycol) and deposited on the second substrate 752 to form the oxygen releasing calibrant layer 754. In some embodiments, the calibrant layer 754 may be covered with a hydrophobic membrane (e.g., silicone-polycarbonate copolymer) or any other protective layer described herein (e.g., the protective layer 128/228/440/540). In some embodiments, the oxygen releasing molecule may be encapsulated in a controlled release polymer (e.g., an acrylamide polymer derivative).

The controller generates the calibrant optical signal so as to urge the calibrant layer 754 to release the predetermined amount of oxygen, thereby raising an oxygen concentration in proximity of the oxygen sensor 710 to a predetermined higher oxygen concentration. The controller may determine a higher calibration parameter of the oxygen sensor 710 corresponding to the predetermined higher oxygen concentration. The controller calibrates the oxygen sensor 710 based on the higher calibration parameter.

In some embodiments, the calibrant layer 754 may be formulated to scavenge oxygen in response to the calibrant optical signal. The calibrant layer 754 may include a heat or light sensitive oxygen scavenger. For example, the calibrant layer 754 may include furfuryl alcohol as the oxygen scavenger which also forms the calibrant layer 754 along with a sensitizer dye (e.g., Rose Bengal or Tetraphenyl porphyrin) in equilibrium with oxygen. The oxygen scavenging calibrant layer 754 may only be active when exposed to light so that the calibrant layer 754 selectively scavenges oxygen when exposed to light. The oxygen scavenging by the calibrant layer 754 may proceed as follows:

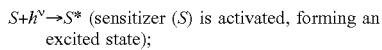

$S+h^\nu \rightarrow S^*$ (sensitizer ($S$) is activated, forming an excited state);

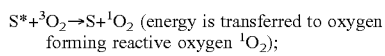

$S^*+{}^3O_2 \rightarrow S+{}^1O_2$ (energy is transferred to oxygen forming reactive oxygen ${}^1O_2$);

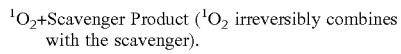

${}^1O_2$+Scavenger Product (${}^1O_2$ irreversibly combines with the scavenger).

To calibrate the oxygen sensor 710, the controller may generate the calibrant optical signal so as to urge the calibrant layer 754 to scavenge oxygen in the proximity of the oxygen sensor 710 and lower an oxygen concentration in proximity of the oxygen sensor 710 to a predetermined lower oxygen concentration. For example, a furfuryl alcohol and tetraphenyl porphyrin based oxygen scavenging calibrant layer may reduce a partial pressure of oxygen from 150 torr to about 35 torr after 10 seconds of exposure to light, and to about 5 torr after another 10 second exposure to light. The controller may determine a lower calibration parameter of the oxygen sensor 710 corresponding to the predetermined lower oxygen concentration. The controller may calibrate the oxygen sensor 710 based on the lower calibration parameter.

In various embodiments, a set of calibration devices may be positioned proximate to the oxygen sensor 710. Each of the calibration device included in the set of calibration devices may be configured to facilitate calibration of the oxygen sensor 710 towards a different parameter, for example temperature and/or oxygen. For example, the set of calibration devices may include a first calibration device configured to release heat, a second calibration device configured to release oxygen and a third calibration device configured to scavenge oxygen. In some embodiments, a single calibration device (e.g., the calibration device 754) may be provided which includes one or more calibrant layers positioned thereon for releasing heat, releasing and/or scavenging oxygen as described herein.

Figure 10:
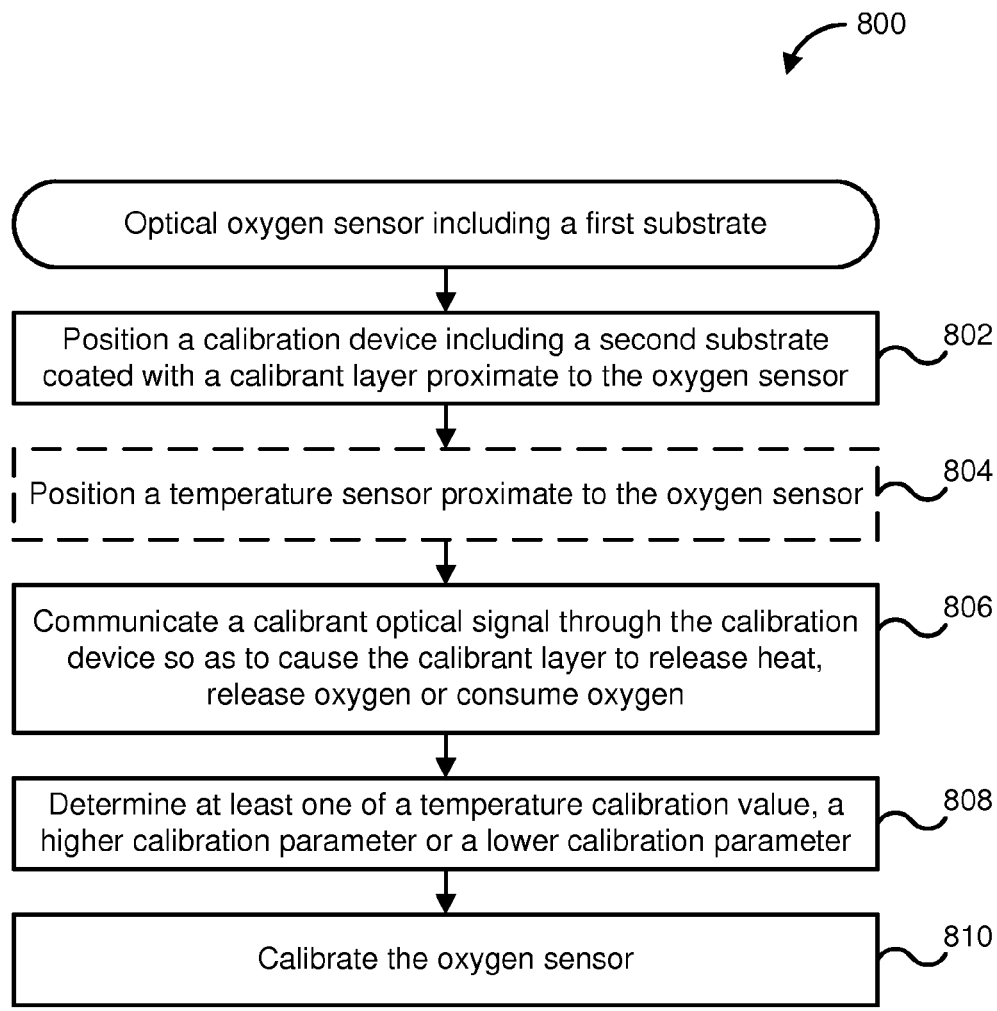
FIG. 10 is a schematic flow diagram of an embodiment of a method for calibrating an oxygen sensor.

FIG. 10 is a schematic flow diagram of an example method 800 for calibrating an optical oxygen sensor including an oxygen sensing layer positioned on a first substrate (e.g., the oxygen sensor 110/210/410/510/710) in-situ. The method 800 includes positioning a calibration device proximate to the oxygen sensor at 802. The calibration device includes a calibrant layer positioned on at least a portion of the second substrate which is structured to communicate a calibrant optical signal. For example, the calibration device 750 is positioned proximate to the oxygen sensor 710.

In some embodiments, the method 800 also includes a positioning a temperature sensor proximate to the oxygen sensor at 804. For example, the temperature sensor 730 may be positioned proximate to the oxygen sensor 710 and used to determine a temperature in the vicinity of the oxygen sensor 710.

A calibrant optical signal is communicated through the second substrate so as to urge the calibrant layer to at least one of release a predetermined amount of heat, release a predetermined amount of oxygen or scavenge oxygen in a proximity of the oxygen sensor at 806. At least one of a temperature calibration value, a higher calibration parameter or a lower calibration parameter is determined at 808. The temperature calibration value, the higher calibration parameter and/or the lower calibration parameter are used to calibrate the oxygen sensor at 810.

For example, the calibrant layer (e.g., the calibrant layer 754) may be formulated to release a predetermined amount of heat in response to the calibrant optical signal so as to raise a temperature of the oxygen sensing layer (e.g., the oxygen sensing layer 120/220/420/520/720) to a predetermined temperature. A temperature dependency value of the optical parameter is determined based on the predetermined temperature. The temperature dependency value is compared to a known optical parameter value at the predetermined temperature so as to determine a temperature calibration value, and the oxygen sensor (e.g., the oxygen sensor 110/210/410/510/710) is calibrated based on the temperature calibration value.

In some embodiments, the calibrant layer (e.g., the calibrant layer 754) is formulated to release a predetermined amount of oxygen in response to the calibrant optical signal so as to raise an oxygen concentration in proximity of the oxygen sensor to a predetermined higher oxygen concentration. In such embodiments, the method 800 may include determining the higher calibration parameter of the oxygen sensor (e.g., the oxygen sensor 110/210/410/510/710) corresponding to the predetermined higher oxygen concentration. The oxygen sensor is calibrated based on the higher calibration parameter.

In some embodiments, the calibrant layer may be formulated to scavenge oxygen in response to the calibrant optical signal so as to lower an oxygen concentration in proximity (e.g., within a distance of 1 inch, 2 inch or 3 inches) of the oxygen sensor (e.g., the oxygen sensor 110/210/410/510/710) to a predetermined lower oxygen concentration. The method 800 may further include determining the lower calibration parameter of the oxygen sensor corresponding to the predetermined lower oxygen concentration, and calibrating the oxygen sensor based on the lower calibration parameter.

Figure 11:
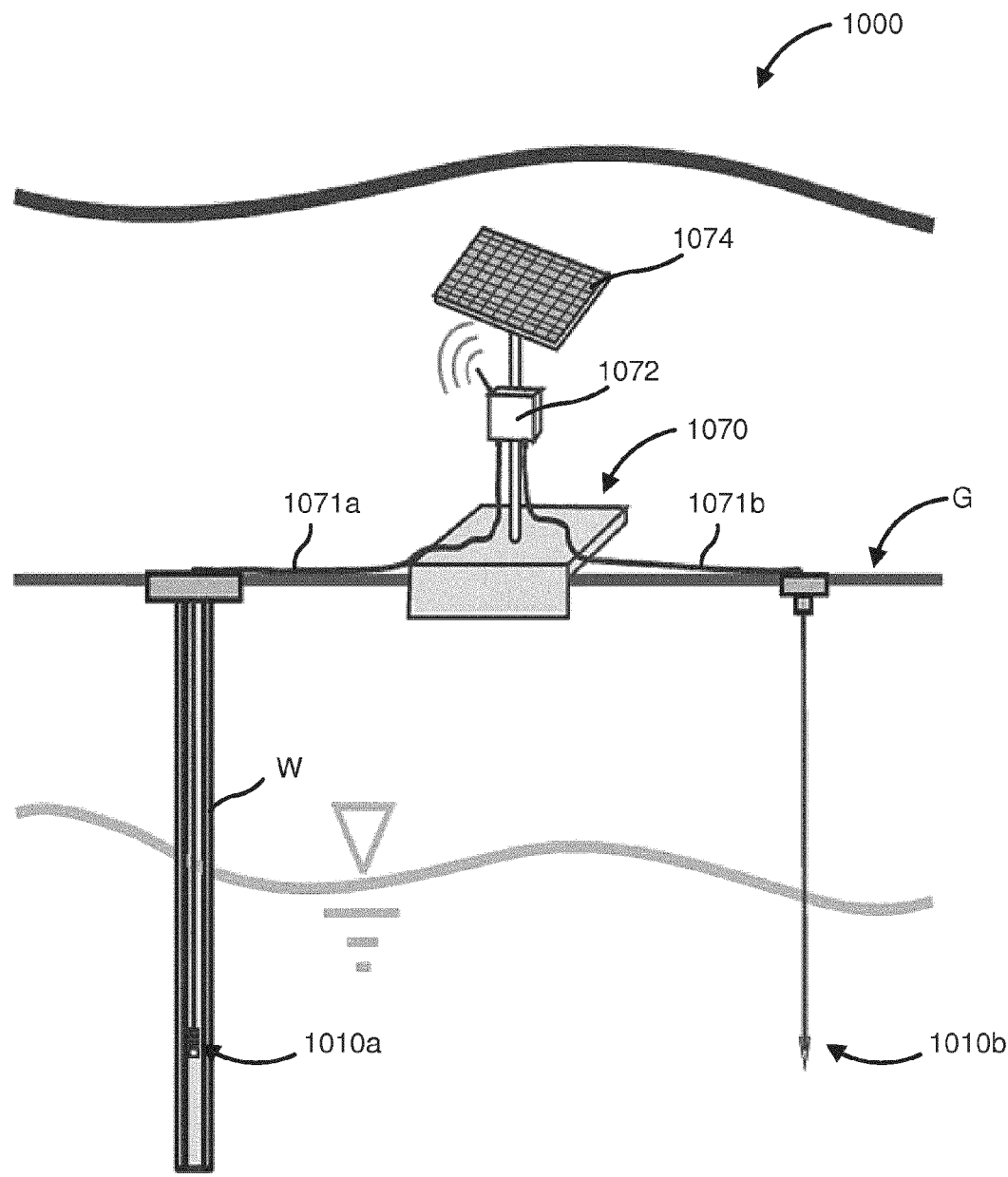
FIG. 11 is a schematic illustration of an optical sensing system for remote sensing of one or more parameters of soil.

The optical sensors described herein, for example, the oxygen sensors 110/210/710, the optical sensors 410/510 or any other optical sensors described herein may be included in a remote sensing system for monitoring soil quality. For example, FIG. 11 is a schematic illustration of a soil sensing system 1000 according to an embodiment. The soil sensing system includes a first optical sensor 1010*a* and a second optical sensor 1010*b* each of which is communicatively coupled to a controller 1070.

The first optical sensor 1010*a* and the second optical sensor 1010*b* can include any of the optical sensors described herein (e.g., the oxygen sensor 110/210/710 or the optical sensor 410/510). Each of the first optical sensor 1010*a* and the second optical sensor 1010*b* is configured to measuring a parameter (e.g., oxygen) in subsurface soil beneath ground G at a particular geolocation. For example, the first optical sensor 1010*a* and the second optical sensor 1010*b* can be configured to measure a concentration of oxygen, ion concentration, nitrogen concentration or measure any desired suitable parameter of the subsurface soil or groundwater present in the subsurface soil beneath the ground G.

The first optical sensor 1010*a* is positioned within a well W penetrating into the soil G. The well W can include an existing monitoring well or a fresh well bored into the ground G. Groundwater can diffuse into the well W and contact the first optical sensor 1010*a*, thereby enabling the first optical sensor 1010*a* to measure one or more parameters of the groundwater (e.g., oxygen concentration).

On the other hand, the second optical sensor 1010*b* is inserted directly into the ground G into the subsurface soil. Groundwater may diffuse directly to the second optical sensor 1010*a* so that the second optical sensor 1010*b* may monitor one or more parameters of the groundwater or the subsurface soil beneath the ground G. In such embodiments, a protective layer positioned on a tip of the second optical sensor 1010*b* (e.g., the protective layer 440*a/b* or 540) inserted into the ground G may also be structured to protect the tip of the second optical sensor 1010*b* and, thereby a sensing layer (e.g., the oxygen sensing layer 120/220 or the optical sensing layer 420/520) of the second optical sensor 1010*b* from physical damage due to inserting into the subsurface soil. The protective layer may allow the water to diffuse to the oxygen sensing layer while protecting the oxygen sensing layer from silt and other soil particles.

In some embodiment, the second optical sensor 1010*b* may be inserted into the ground G by attaching a tool string device such as a geoprobe to the second optical sensor 1010*b* for driving the second optical sensor into the ground G, or lowered into a hollow rod of a geoprobe (e.g., a rod or a drill) once the geoprobe or any other suitable instrument is inserted to a desired depth into the subsurface soil beneath the ground G. Once inserted, the geoprobe or any other drilling instrument may be removed allowing the subsurface soil to refill the opening (e.g., a hole or annular opening) created from the inserting the geoprobe into the subsurface soil.

The first optical sensor 1010*a* and the second optical sensor 1010*b* are communicatively coupled to the controller 1070 via a first conduit 1071*a* or a second conduit 1071*b* (collectively referred to herein as "the conduits 1071"), respectively. The conduits 1071 may include electrical leads configured to communicate electrical signals indicative of electrical parameters measured by each of the first optical sensor 1010*a* and the second optical sensor 1010*b* to the controller 1070. In some embodiments, the conduits 1071 may include optical conduits (e.g., fiber optic cables) configured to communicate optical signals from the first and second optical sensors 1010*a/b* to the controller 1070. In some embodiments, the electrical or optical signals from the optical sensors 1010*a/b* may be wirelessly communicated to the controller 1070, for example using Bluetooth®, low power Bluetooth®, Wi-Fi or any other suitable wireless communication protocol.

The controller 1070 may be configured to convert the optical signals into electrical signals (e.g., AC or DC signals) which may be analyzed to determine a concentration of one or more parameters (e.g., oxygen content) of the groundwater and/or subsurface soil. In various embodiments, the optical sensors 1010*a/b* or any number of optical sensors can be multiplexed through a multiplexer (not shown) and sequenced to allow the plurality of optical sensors to be communicatively coupled to the controller 1070. In other embodiments, individual dedicated controllers may be provided for each optical sensor included in the plurality of optical sensors.

In various embodiments, the controller 1070 may be substantially similar to the controller 170 or any other controller described herein. The controller 1070 may include communications circuitry 1072 configured to communicate signals corresponding to the parameter of the subsurface soil or groundwater determined by the first and second optical sensors 1010*a/b* to a central computer, a remote server or a remote data logger, for example for off-site analysis and storage. The communications circuitry 1072 may include electrical leads or wireless communication circuitry (e.g., Bluetooth®, low power Bluetooth®, Wi-Fi or any other suitable wireless communication circuitry) for wirelessly communicating signals from the controller 1070 to the central computer, the remote server or the remote data logger.

A power supply 1074 is also coupled to the controller 1070 and configured to provide electrical power to the controller 1070. For example, the power supply can include a solar panel or a wind turbine to produce power for operating the controller 1070 on-site. The power supply 1074 may also include a rechargeable battery (e.g., Li-ion or lead acid battery) configured to store electrical power produced by the solar panel or wind turbine included in the power supply 1074.

Figure 12:
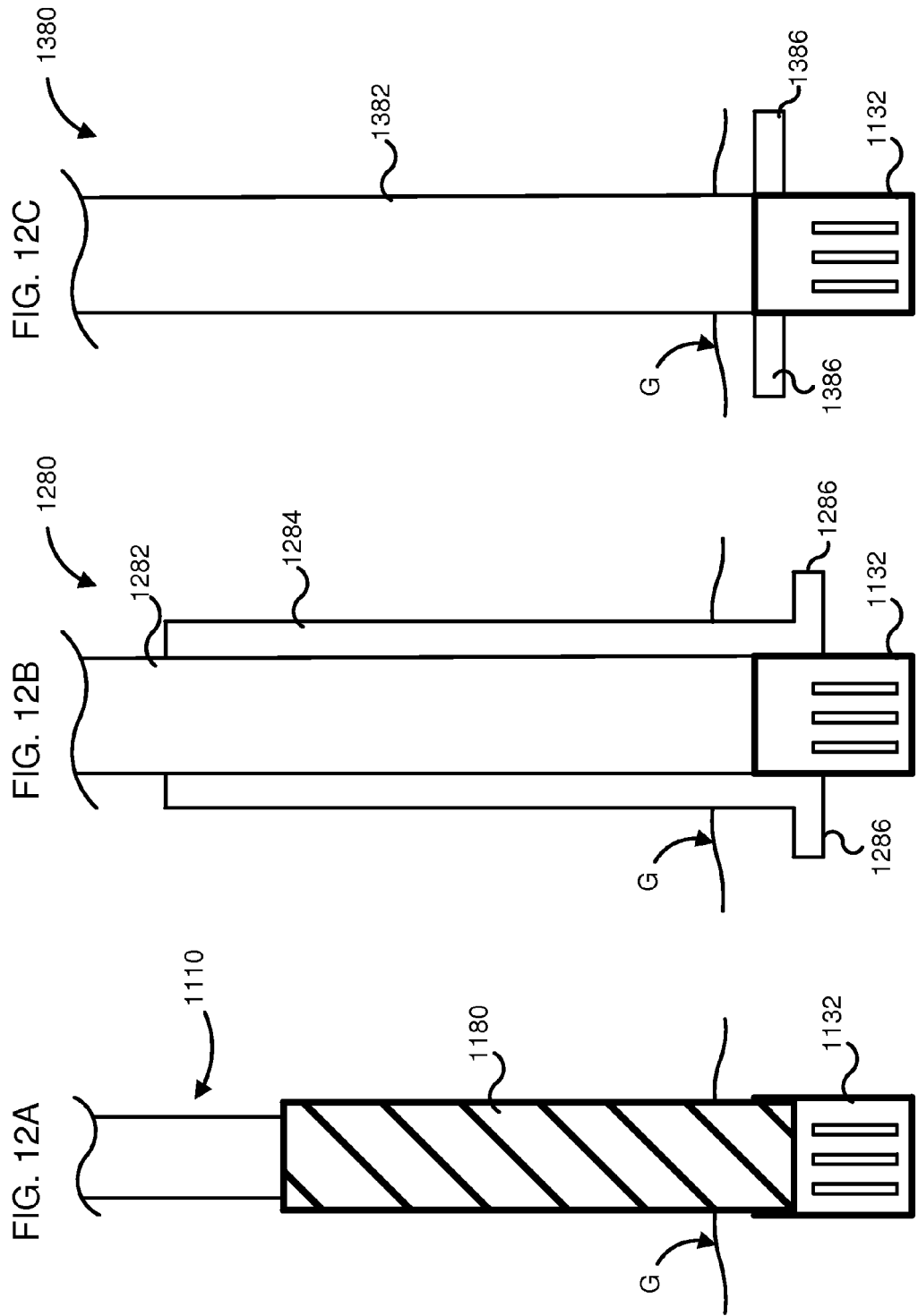
FIG. 12A-C are schematic illustrations of various sheathing assemblies for physically protecting an optical sensor for inserting into soil.

In some embodiments, a substrate of the optical sensor configured to be inserted into the ground may be enclosed in a protective sheath to protect the substrate and/or the tip of the optical sensor from damage during insertion. For example, FIG. 12A is a schematic illustration of a sheathing assembly 1180. The sheathing assembly 1180 includes a hollow cable, for example a metal armored cable. An optical sensor 1110 (e.g., the oxygen sensor 110/210/710 or the optical sensor 410/510) is positioned within an annular channel defined by the cable 1180.

In this manner, the cable 1180 forms a protective sheath around the optical sensor 1110 so as to increase robustness of the optical sensor 1110 and to prevent a substrate (e.g., fiber optic cable) of the optical sensor 1110 from damage, for example during insertion of the optical sensor 1110 in loose rock formations. A tip of the optical sensor 1110 is positioned inside a housing 1132. The housing 1132 may be substantially similar to the housing 232/532 or any other housing described herein. The housing 1132 protects the tip of the optical sensor 1110 while allowing groundwater to diffuse or penetrate into an internal volume defined by the housing within which the tip of the optical sensor 1110 including an optical sensing layer (e.g., the oxygen sensing layer 120/220 or the optical sensing layer 420/520) are positioned.

In some embodiments, a protective sheath may be configured to allow removable positioning of an optical sensor within a subsurface soil beneath a ground G. For example, FIG. 12B is a schematic illustration of a sheathing assembly 1280 according to an embodiment. The sheathing assembly 1280 includes a hollow inner tube 1282 within which an optical sensor (e.g., the optical sensor 1110) and any other sensor (e.g. temperature sensor 130/230/730 or the calibration device 750) are positioned. A tip of the optical sensor may be positioned within the housing 1132 as described herein. In some embodiments, a conduit or tube may also be fluidly coupled to the housing 1132 so as to draw groundwater from the subsurface soil, for example in low flow or similar sampling scenarios.

The inner sidewalls of the inner sheath 1282 may have a low coefficient of friction of friction (i.e., is slippery) relative to a substrate of the optical sensors (e.g., a fiber optic cable or a tubing such as a polyimide tubing within which the substrate of the optical sensor or any other sensors included in the optical sensing assembly are encapsulated). For example, a lubricant (e.g., liquid lubricant such as mineral oil or a solid lubricant such as graphite) may be disposed on the inner sidewalls of the outer sheath 1292, or the inner sheath may be formed from a slippery material, e.g., PTFE. The slippery inner sidewalls of the inner sheath 1282 may allow easy insertion and removal of the optical sensors from the inner sheath 1282.

An outer sheath 1284 is positioned around at least a portion of the inner sheath 1282 that is inserted into a ground G. The outer sheath 1284 may be formed from a strong and rigid material (e.g., metals, plastics, etc.) so as to prevent physical damage to the inner sheath 1282 and, thereby the optical sensor or any other sensor positioned therein during insertion into the ground G. A plurality of barbs 1286 are positioned at a distal end of the outer sheath 1284 which is positioned within the ground G. The barbs 1286 may be configured to catch the subsurface soil beneath the ground G so as to allow the optical sensors to be removed from the inner sheath by pulling thereon, while preventing the outer sheath 1284 and/or the inner sheath 1282 from being removed from the ground G.

FIG. 12C is a schematic illustration of another sheathing assembly 1380 according to an embodiment. The sheathing assembly 1380 includes a hollow sheath 1382 within which an optical sensor (e.g., the optical sensor 1180) and any other sensor (e.g. temperature sensor 130/230/730 or the calibration device 750) are positioned. The sheath 1382 may be substantially similar to the inner sheath 1284. A plurality of barbs 1386 are positioned on a distal end of the sheath 1382 positioned into a subsurface soil within a ground G. The barbs 1386 may be configured to catch the subsurface soil beneath the ground G so as to allow the optical sensor to be removed from the sheath 1382 by pulling thereon, while preventing the sheath 1382 from being removed from the ground G.

Any of the sheathing assemblies 1180/1280/1380 or any other sheathing assembly describe herein may also be structure to include other features or configured to house other sensors. For example, any of the sheathing assemblies described herein may be structured to house cables, fibers, vents or other sensors (e.g., pressure sensors) therein.

Figure 13:
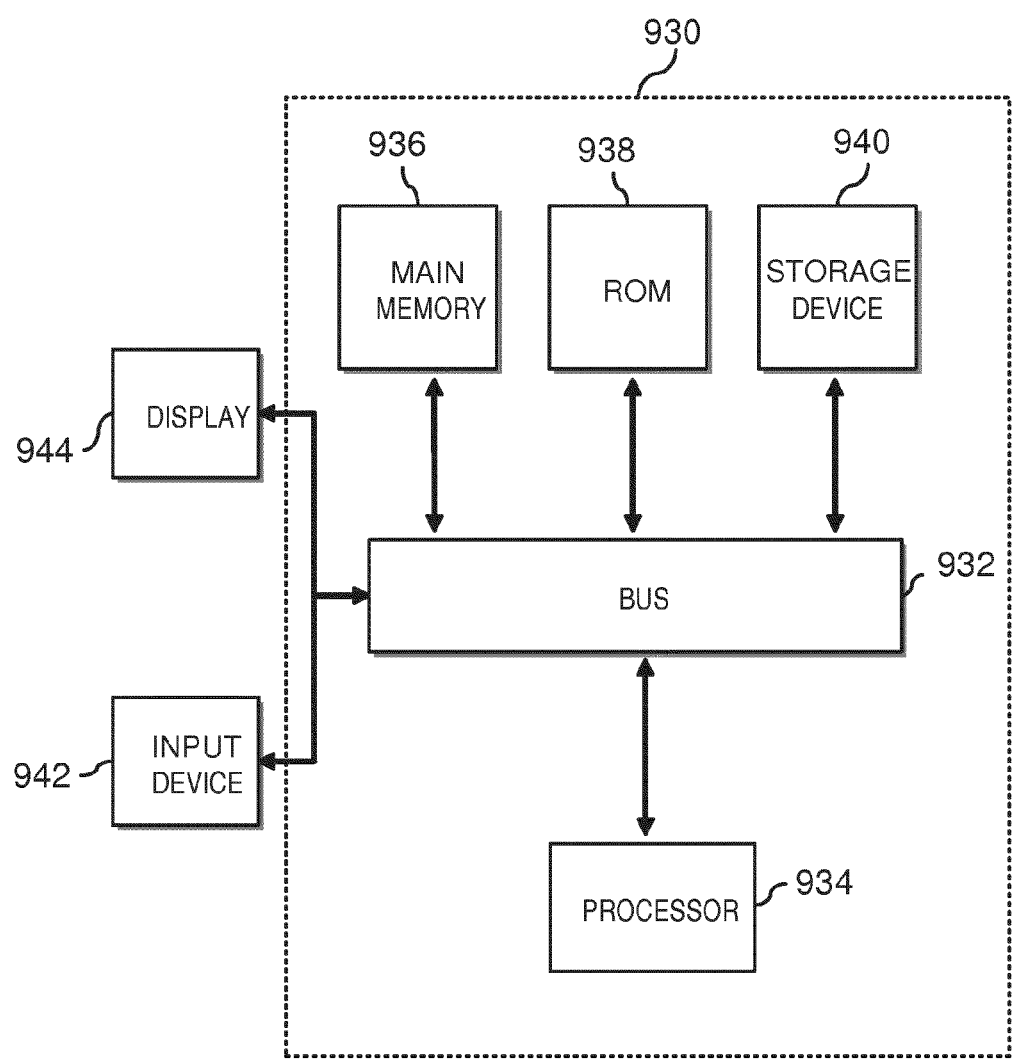
FIG. 13 is a schematic block diagram of a computing device which can be used as a controller shown in FIG. 1 or any other controller described herein.

Any of the methods defined herein can be executed on a stored on a computer readable medium and executed by a computing device specifically programmed to execute the instructions stored on the computer readable medium. FIG. 13 is a block diagram of a computing device 930 in accordance with an illustrative implementation. The computing device 930 includes a bus 932 or other communication component for communicating information and a processor 934 or processing circuit coupled to the bus 932 for processing information. The computing device 930 can also include one or more processors 934 or processing circuits coupled to the bus 932 for processing information. The computing device 930 also includes a main memory 936, such as a random access memory (RAM) or other dynamic storage device, coupled to the bus 932 for storing information, and instructions to be executed by the processor 934. Main memory 936 can also be used for storing position information, temporary variables, or other intermediate information during execution of instructions by the processor 934. The computing device 930 may further include a read only memory (ROM) 938 or other static storage device coupled to the bus 932 for storing static information and instructions for the processor 934. A storage device 940, such as a solid-state device, magnetic disk or optical disk, is coupled to the bus 932 for persistently storing information and instructions.

The computing device 930 may be coupled via the bus 932 to a display 944, such as a liquid crystal display, or active matrix display, for displaying information to a user. An input device 942, such as a keyboard including alphanumeric and other keys, may be coupled to the bus 932 for communicating information and command selections to the processor 934. In another implementation, the input device 942 has a touch screen display 944. The input device 942 can include a cursor control, such as a mouse, a trackball, or cursor direction keys, for communicating direction information and command selections to the processor 934 and for controlling cursor movement on the display 944.

According to various implementations, the processes and methods described herein can be implemented by the computing device 930 in response to the processor 934 executing an arrangement of instructions contained in main memory 936. Such instructions can be read into main memory 936 from another non-transitory computer-readable medium, such as the storage device 940. Execution of the arrangement of instructions contained in main memory 936 causes the computing device 930 to perform the illustrative processes described herein. One or more processors in a multi-processing arrangement may also be employed to execute the instructions contained in main memory 936. In alternative implementations, hard-wired circuitry may be used in place of or in combination with software instructions to effect illustrative implementations. Thus, implementations are not limited to any specific combination of hardware circuitry and software.

Although an example computing device has been described in FIG. 13, implementations described in this specification can be implemented in other types of digital electronic circuitry, or in computer software, firmware, or hardware, including the structures disclosed in this specification and their structural equivalents, or in combinations of one or more of them.

Implementations described in this specification can be implemented in digital electronic circuitry, or in computer software, firmware, or hardware, including the structures disclosed in this specification and their structural equivalents, or in combinations of one or more of them. The implementations described in this specification can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described in this specification can be performed by a data processing apparatus on data stored on one or more computer-readable storage devices or received from other sources. The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the terms "example" or "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any embodiments or of what may be claimed, but rather as descriptions of features specific to particular implementations of particular embodiments. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. An oxygen sensing system, comprising:
    an oxygen sensor comprising:
        a substrate structured to communicate optical signals;
        an oxygen sensing layer disposed on the substrate, the oxygen sensing layer comprising an oxygen sensing molecule disposed in a matrix, the oxygen sensing molecule formulated to be in a first unexcited state, the oxygen sensing molecule further formulated to:
            (a) be excited in response to a first optical signal so as to move into a second state,
            (b) be quenched in the second state by oxygen present in a sample in contact with the oxygen sensor, and
            (c) emit a second optical signal different from the first optical signal, an optical parameter of the second optical signal corresponding to an amount of the oxygen present in the sample;
        a protective layer disposed on the oxygen sensing layer, the protective layer including at least one of i) an oleophobic layer configured to protect the oxygen sensing layer from hydrocarbons and organic solvents, and ii) an anti-fouling layer configured to protect the oxygen sensing layer from fouling;
    a housing defining an internal volume, at least one opening defined on the sidewalls of the housing, the opening configured to allow the sample to infiltrate the housing therethrough;
    a plurality of fouling-resistant particles positioned within the internal volume of the housing, the plurality of fouling-resistant particles including an anti-fouling agent, wherein at least a portion of the oxygen sensor including the oxygen sensing layer is positioned within the internal volume defined by the housing, the portion of the oxygen sensor surrounded by the plurality of fouling-resistant particles so as to protect at least the portion of the oxygen sensor from fouling; and
    a controller optically coupled to the substrate, the controller structured to generate the first optical signal and communicate the first optical signal to the oxygen sensing layer via the substrate, the controller further configured to receive the second optical signal via the substrate and analyze the optical parameter of the second optical signal to determine a concentration of the oxygen in the sample.

2. The oxygen sensing system of claim 1, further comprising:
    a temperature sensor configured to measure a temperature of the sample.

3. The oxygen sensing system of claim 1, wherein the substrate includes a fiber optic cable.

4. The oxygen sensing system of claim 1, wherein the oxygen sensing molecule comprises an oxygen sensitive dye and the matrix includes a sol-gel.

5. The oxygen sensing system of claim 4, wherein the oxygen sensitive dye includes at least one of platinum meso-tetra(pentafluorophenyl)porphine, palladium meso-tetra(pentafluorophenyl)porphine, gadolinium meso-tetra(pentafluorophenyl)porphine, platinum octaethylporphine, palladium octaethylporphine, gadolinium octaethylporphine, platinum meso-tetraphenylporphine, platinum tetra(pentafluorophenyl)porpholactone, palladium meso-tetraphenylporphine, gadolinium meso-tetraphenylporphine, ruthenium tris(4,7-diphenyl-1,1.phenanthroline)$Cl_2$, osmium tris(bathophenanthroline)dichloride, iridium(III) bis(4-phenylthieno[3,2-c] pyridinato-N,C2')acetylacetonate.

6. The oxygen sensing system of claim 1, wherein the oxygen sensing layer further comprises:
    a photo stabilizer formulated to scavenge oxygen from the oxygen sensing layer.

7. The oxygen sensing system of claim 1, wherein the oleophobic layer includes a cross-linked amorphous fluoropolymer.

8. The oxygen sensing system of claim 1, wherein the oleophobic layer includes a cross-linked sol-gel mixture.

9. The oxygen sensing system of claim 1, wherein the anti-fouling layer comprises at least one of N-alkylated poly(4-vinyl-pyridine), N-halomine or an anti-fouling paint.

10. The oxygen sensing layer of claim 1, wherein the protective layer is hydrophobic.

11. The oxygen sensing system of claim 1, further comprising:
    a calibration device positioned proximate to the oxygen sensor, the calibration device including:

a second substrate structured to communicate a calibrant optical signal; and a calibrant layer positioned on at least a portion of the second substrate, the calibrant layer responsive to the calibrant optical signal so as to at least one of release a predetermined amount of heat, release a predetermined amount of oxygen, or scavenge oxygen in a proximity of the oxygen sensor.

12. The oxygen sensing system of claim 11, wherein the calibrant layer is formulated to release a predetermined amount of heat in response to the calibrant optical signal, and wherein the controller is further configured to:

generate the calibrant optical signal so as to urge the calibrant layer to release the predetermined amount of heat so as to raise a temperature of the oxygen sensing layer to a predetermined temperature;

determine a temperature dependency value of the optical parameter based on the predetermined temperature;

compare the temperature dependency value to a known optical parameter value at the predetermined temperature so as to determine a temperature calibration value; and calibrate the oxygen sensor based on the temperature calibration value.

13. The oxygen sensing system of claim 11, wherein the calibrant layer is formulated to release a predetermined amount of oxygen in response to the calibrant optical signal, and wherein the controller is further configured to:

generate the calibrant optical signal so as to urge the calibrant layer to release the predetermined amount of oxygen so as to raise an oxygen concentration in proximity of the oxygen sensor to a predetermined higher oxygen concentration;

determine a higher calibration parameter of the oxygen sensor corresponding to the predetermined higher oxygen concentration; and calibrate the oxygen sensor based on the higher calibration parameter.

14. The oxygen sensing system of claim 11, wherein the calibrant layer is formulated to scavenge oxygen in response to the calibrant optical signal, and wherein the controller is further configured to:

generate the calibrant optical signal so as to urge the calibrant layer to scavenge oxygen in the proximity of the oxygen sensor and lower an oxygen concentration in proximity of the oxygen sensor to a predetermined lower oxygen concentration;

determine a lower calibration parameter of the oxygen sensor corresponding to the predetermined lower oxygen concentration; and calibrate the oxygen sensor based on the lower calibration parameter.

15. An oxygen sensor, comprising:

a substrate structured to communicate optical signals;

an oxygen sensing layer disposed on the substrate, the oxygen sensing layer comprising an oxygen sensing molecule disposed in a matrix, the oxygen sensing molecule formulated to be in a first unexcited state, the oxygen sensing molecule further formulated to:

(a) be excited in response to a first optical signal to move into a second state, (b) be quenched in the second state by oxygen present in a sample in contact with the oxygen sensor, and (c) emit a second optical signal different from the first optical signal, an optical parameter of the second optical signal corresponding to an amount of the oxygen present in the sample; and a protective layer disposed on the oxygen sensing layer, the protective layer including an oleophobic layer, which includes a cross-linked sol-gel mixture, configured to protect the oxygen sensing layer from hydrocarbons and organic solvents.

16. The oxygen sensor of claim 15, wherein the substrate includes a fiber optic cable.

17. The oxygen sensor of claim 15, wherein the oxygen sensing molecule comprises an oxygen sensitive dye and the matrix includes a sol-gel.

18. The oxygen sensor of claim 17, wherein the oxygen sensitive dye includes at least one of platinum meso-tetra(pentafluorophenyl)porphine, palladium meso-tetra(pentafluorophenyl)porphine, gadolinium meso-tetra(pentafluorophenyl)porphine, platinum octaethylporphine, palladium octaethylporphine, gadolinium octaethylporphine, platinum meso-tetraphenylporphine, platinum tetra(pentafluorophenyl)porpholactone, palladium meso-tetraphenylporphine, gadolinium meso-tetraphenylporphine, ruthenium tris(4,7-diphenyl-1,1.phenanthroline)$Cl_2$, osmium tris(bathophenanthroline)dichloride, iridium(III) bis(4-phenylthieno[3,2-c]pyridinato-N,C2')acetylacetonate.

19. The oxygen sensor of claim 15, wherein the oleophobic layer comprises a cross-linked amorphous fluoropolymer.

20. The oxygen sensor of claim 15, wherein the anti-fouling layer comprises at least one of N-alkylated poly (4-vinyl-pyridine), N-halomine or an anti-fouling paint.

21. An oxygen sensing system, comprising:

an oxygen sensor comprising:

a substrate structured to communicate optical signals;

an oxygen sensing layer disposed on the substrate, the oxygen sensing layer comprising an oxygen sensing molecule disposed in a matrix, the oxygen sensing molecule formulated to be in a first unexcited state, the oxygen sensing molecule further formulated to:

(a) be excited in response to a first optical signal so as to move into a second state, (b) be quenched in the second state by oxygen present in a sample in contact with the oxygen sensor, and (c) emit a second optical signal different from the first optical signal, an optical parameter of the second optical signal corresponding to an amount of the oxygen present in the sample;

a protective layer disposed on the oxygen sensing layer, the protective layer including at least one of i) an oleophobic layer configured to protect the oxygen sensing layer from hydrocarbons and organic solvents, and ii) an anti-fouling layer configured to protect the oxygen sensing layer from fouling;

a calibration device positioned proximate to the oxygen sensor, the calibration device including:

a second substrate structured to communicate a calibrant optical signal; and a calibrant layer positioned on at least a portion of the second substrate, the calibrant layer responsive to the calibrant optical signal so as to at least one of release a predetermined amount of heat, release a predetermined amount of oxygen, or scavenge oxygen in a proximity of the oxygen sensor;

a controller optically coupled to the substrate, the controller structured to generate the first optical signal and communicate the first optical signal to the oxygen sensing layer via the substrate, the controller further configured to receive the second optical signal via the substrate and analyze the optical parameter of the second optical signal to determine a concentration of the oxygen in the sample.

22. The oxygen sensing system of claim 21, wherein the calibrant layer is formulated to release a predetermined amount of heat in response to the calibrant optical signal, and wherein the controller is further configured to:
generate the calibrant optical signal so as to urge the calibrant layer to release the predetermined amount of heat so as to raise a temperature of the oxygen sensing layer to a predetermined temperature;
determine a temperature dependency value of the optical parameter based on the predetermined temperature;
compare the temperature dependency value to a known optical parameter value at the predetermined temperature so as to determine a temperature calibration value; and
calibrate the oxygen sensor based on the temperature calibration value.

23. The oxygen sensing system of claim 21, wherein the calibrant layer is formulated to release a predetermined amount of oxygen in response to the calibrant optical signal, and wherein the controller is further configured to:
generate the calibrant optical signal so as to urge the calibrant layer to release the predetermined amount of oxygen so as to raise an oxygen concentration in proximity of the oxygen sensor to a predetermined higher oxygen concentration;
determine a higher calibration parameter of the oxygen sensor corresponding to the predetermined higher oxygen concentration; and
calibrate the oxygen sensor based on the higher calibration parameter.

24. The oxygen sensing system of claim 21, wherein the calibrant layer is formulated to scavenge oxygen in response to the calibrant optical signal, and wherein the controller is further configured to:
generate the calibrant optical signal so as to urge the calibrant layer to scavenge oxygen in the proximity of the oxygen sensor and lower an oxygen concentration in proximity of the oxygen sensor to a predetermined lower oxygen concentration;
determine a lower calibration parameter of the oxygen sensor corresponding to the predetermined lower oxygen concentration; and
calibrate the oxygen sensor based on the lower calibration parameter.

* * * * *